US009416392B2

(12) United States Patent
Lukaszewicz et al.

(10) Patent No.: US 9,416,392 B2
(45) Date of Patent: Aug. 16, 2016

(54) DIAGNOSIS OF BACTERIAL MENINGITIS BASED ON THE MEASURE OF ROS PRODUCTION IN A SAMPLE OF CEREBROSPINAL FLUID

(75) Inventors: Anne-Claire Lukaszewicz, Chantilly (FR); Ingrid Ouanounou, Paris (FR); Didier Payen De La Garanderie, Paris (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 13/811,860

(22) PCT Filed: Jul. 26, 2011

(86) PCT No.: PCT/IB2011/053329
§ 371 (c)(1),
(2), (4) Date: Feb. 26, 2013

(87) PCT Pub. No.: WO2012/014156
PCT Pub. Date: Feb. 2, 2012

(65) Prior Publication Data
US 2013/0157301 A1    Jun. 20, 2013

(30) Foreign Application Priority Data

Jul. 26, 2010  (EP) ..................................... 10290421

(51) Int. Cl.
*C12Q 1/04* (2006.01)
*G01N 33/00* (2006.01)
*G01N 33/50* (2006.01)
*G01N 33/84* (2006.01)

(52) U.S. Cl.
CPC .............. *C12Q 1/04* (2013.01); *G01N 33/5091* (2013.01); *G01N 33/84* (2013.01); *G01N 2800/52* (2013.01)

(58) Field of Classification Search
CPC ................ G01N 2333/90209; G01N 2800/14; G01N 33/5088; G01N 2500/04; G01N 33/5055; G01N 33/5064; G01N 33/564; G01N 33/566; G01N 33/92; G01N 2333/726; G01N 2800/32; G01N 2800/325; G01N 33/5005; G01N 33/5038; G01N 2800/52; G01N 33/5091; G01N 33/84; C12Q 1/04
See application file for complete search history.

(56) References Cited

U.S. PATENT DOCUMENTS 8,173,598 B2 *  5/2012  Sroussi .............. A61K 38/1709
                                                 514/15.1

FOREIGN PATENT DOCUMENTS

DE          10351250        6/2005

OTHER PUBLICATIONS

Nau et al Trends Neurosci. 2002; 25(1):38-45.*
Samuni et al Free Radic Biol Med. 1991 Abstract only.*
Perry,et al Thorax 1994;49:676-683.*
Blagosklonny, M.V., et al.;"*Defects in p21WAF1/CIP1, Rb, and c-myc signaling in phorbol ester-resistant cancer cells*;" Cancer Res, vol. 57, No. 2; pp. 320-325; dated Jan. 1997; retrieved on Feb. 22, 2013 from <http://pubget.com/pdf/9000576>.
Bota, D.P., et al.; "*Ventriculostomy-related infections in critically ill patients: a 6-year experience*;" JNeurosurg, vol. 103, No. 3; pp. 468-472; dated Sep. 2005.
Bottcher, T., et al.; "*Rifampin Reduces Production of Reactive Oxygen Species of Cerebrospinal Fluid Phagocytes and Hippocampal Neuronal Apoptosis in Experimental Streptococcus pneumonia Meningitis*;" The Journal of Infectious Diseases, vol. 181, No. 6; pp. 2091-2098; dated Jun. 2000.
Cassatella, M.A., et al.; "*Molecular basis of interferon-gamma and lipopolysaccharide enhancement of phagocyte respiratory burst capability. Studies on the gene expression of several NADPH oxidase components;" J Biol Chem, vol. 265, No. 33; pp. 20241-20246; dated Nov. 1990; retrieved on Feb. 22, 2013 from <http://www.researchgate.net/publication/20981757_Molecular_basis_of_interferon-gamma_and_lipopolysaccharide_enhancement_of_phagocyte_respiratory_burst_capability._Studies_on_the_gene_expression_of_several_NADPH_oxidase_components >.
Chung, L., et al.; "*Kinetic change of oxidative stress in cerebrospinal fluid of mice infected with Angiostrongylus cantonensis*;" Redox Report, vol. 15, No. 1; pp. 43-48; dated Jan. 2010.
Druel, B., et al.; "*Aseptic meningitis after neurosurgery: a demonstration of bacterial involvement*;" Clin Microbiol Infect, vol. 1, No. 4; pp. 230-234; dated Jun. 1996.
Fay, A.J., et al.; "*SK channels mediate NADPH oxidase-independent reactive oxygen species production and apoptosis in granulocytes*;" Proc Natl Acad Sci USA, vol. 103, No. 46; pp. 17548-17553;dated Nov. 2006; retrieved on Feb. 22, 2013 from < http://www.pnas.org/content/103/46/17548.full.pdf+html>.
Forgacs, P., et al.; "*Characterization of chemical meningitis after neurological surgery*;" Clin Infect Dis, vol. 32, No. 2; pp. 179-185; dated Jan. 2001; retrieved on Feb. 22, 2013 from <http://cid.oxfordjournals.org/content/32/2/179.full.pdf+html>.

(Continued)

*Primary Examiner* — Padma V Baskar
(74) *Attorney, Agent, or Firm* — Alston & Bird LLP

(57) ABSTRACT

The present invention pertains to a method for in vitro diagnosing a bacterial infection in a biological fluid selected amongst cerebrospinal fluid, ascitic fluid, pericardial fluid, pleural fluid, urine and synovial fluid, based on the measure, in a sample of said fluid, of the production of reactive oxygen species (ROS); a high level of ROS production is indicative of the presence of activated polymorphonuclear neutrophils (PMNs) in said fluid, which in turn is a hallmark of bacterial infection.

8 Claims, 8 Drawing Sheets

(56) References Cited

OTHER PUBLICATIONS

Freitas, M., et al.; "*Optical probes for detection and quantification of neutrophils' oxidative burst. A review*;" Analytica Chimica Acta, vol. 649, No. 1; pp. 8-23; dated Jul. 2009.

Hader, W.J., et al.; "*The value of routine cultures of the cerebrospinal fluid in patients with external ventricular drains*;" Neurosurgery, vol. 46, No. 5; pp. 1149-1153; dated May 2000.

Helen, H., et al.; "*Cerebrospinal fluid biomarkers in bacterial meningitis*;" J. Lab. Med., vol. 33, No. 6; pp. 321-331; dated Dec. 2009.

Holloway, K.L., et al.; "*Ventriculostomy infections: the effect of monitoring duration and catheter exchange in 584 patients*;" JNeurosurg, vol. 85, No. 3; pp. 419-424; dated Sep. 1996.

International Search Report and Written Opinion of the Searching Authority for Application No. PCT/IB2011/053329; dated Mar. 28, 2012.

Kerkhoff, C., et al.; "*The arachidonic acid-binding protein S100A8/A9 promotes NADPH oxidase activation by interaction with p67phox and Rac-2*;" Faseb J, vol. 19, No. 3; pp. 467 ¬ 469; dated Mar. 2005; retrieved on Feb. 22, 2013 from < http://pubget.com/pdf/15642721>.

Klassen, D.K., et al.; *Activation of monocyte and granulocyte antibody-dependent cytotoxicity by phorbol myristate acetate*; Infect Immun, vol. 35, No. 3; pp. 818-825; dated Mar. 1982; retrieved on Feb. 22, 2013 from <http://www.ncbi.nlm.nih.gov/pmc/articles/PMC351121/ >.

Leib, S.L., et al.; "*Predictive value of cerebrospinal fluid (CSF) lactate level versus CSF/blood glucose ratio for the diagnosis of bacterial meningitis following neurosurgery*;" Clin Infect Dis, vol. 29, No. 1; pp. 69-74; dated Jul. 1999; retrieved on Feb. 22, 2013 from <cid.oxfordjournals.org/content/29/1/69.full.pdf>.

Li, Y., et al.; "*Diphenyleneiodonium, an NAD(P)H oxidase inhibitor, also potently inhibits mitochondrial reactive oxygen species production*;" Biochem Biophys Res Commun, vol. 253, No. 2; pp. 295-299; dated Dec. 1998.

Liang, K.Y., et al.; "*Longitudinal Data Analysis Using Generalized Linear Models*;" Biometrika, vol. 73, No. 1 ; pp. 13-22; dated Oct. 1986; retrieved on Feb. 22, 2013 from <http://www.google.com/search?q=Longitudinal+Data+Analysis+Using+Generalized+Linear+Models&rls=com.microsoft:en-us&ie=UTF-8&oe=jhUTF-8&startIndex=&start Page=1>.

Lozier, A.P., et al.; "*Ventriculostomy-related infections: a critical review of the literature*;" Neurosurgery, vol. 51, No. 1; pp. 170-181; discussion 181-172; dated Jul. 2002.

Lundqvist-Gustafsson, H., et al.; "*Activation of the granule pool of the NADPH oxidase accelerates apoptosis in human neutrophils*;" J Leukoc Biol, vol. 65, No. 2; pp. 196-204; dated Feb. 1999; retrieved on Feb. 22, 2013 from <www.jleukbio.org/content/65/2/196.full.pdf>.

Marshall, J.C., et al.; "*Biomarkers of sepsis*;" Crit Care Med, vol. 37, No. 7; pp. 2290-2298; dated Jul. 2009.

Mayhall, C.G., et al.; "*Ventriculostomy-related infections. A prospective epidemiologic study*;" N Engl J Med, vol. 310, No. 9; pp. 553-559; dated Mar. 1984.

Menezes, C. C., et al.; "*Oxidative Stress in Cerebrospinal Fluid of Patients with Aseptic and Bacterial Meningitis*;" Neurochem. Res., vol. 34, No. 7; pp. 1255-1260; dated Feb. 2009.

Pfausler, B., et al.; "*Cell index—a new parameter for the early diagnosis of ventriculostomy (external ventricular drainage)-related ventriculitis in patients with intraventricular hemorrhage?*" Acta Neurochir (Wien), vol. 146, No. 5; pp. 477-481; dated May 2004.

Piccoli, C., et al.; "*Characterization of mitochondrial and extra-mitochondrial oxygen consuming reactions in human hematopoietic stem cells. Novel evidence of the occurrence of NAD(P)H oxidase activity*;" J Biol Chem, vol. 280, No. 28; pp. 26467-26476; dated Jul. 2005; retrieved on Feb. 25, 2013 from <http://www.google.com/search?q=Characterization+of+mitochondrial+and+extramitochondrial+oxygen+consuming+reactions+in+human+hematopoietic+ stem+cells.+Novel+evidence+of+the+occurrence+of+NAD%28P%29H+oxidase+activity&rls=com.microsoft:en-us&ie=UTF-8&oe=UTF-8&startIndex=&startPage=1>.

Ross, D., et al.; "*Differentiation of aseptic and bacterial meningitis in postoperative neurosurgical patients*;" J Neurosurg, vol. 69, No. 5; pp. 669-674; dated Nov. 1988.

Segal, A.W."*How neutrophils kill microbes*;" Annu Rev Immunol, vol. 23; pp. 197-223; dated 2005; retrieved on Feb. 25, 2013 from <http://www.ncbi.nlm.nih.gov/pmc/articles/PMC2092448/pdf/nihms-1203.pdf>.

Serhan, C.N., et al.;"*Resolution of inflammation: the beginning programs the end*;" Nat Immunol, vol. 6, No. 12; pp. 1191-1197; dated Dec. 2005.

Tavares, W.M., et al.; "*CSF markers for diagnosis of bacterial meningitis in neurosurgical postoperative patients;* " Arq Neuropsiquiatr, vol. 64, No. 3(A); pp. 592-595; dated Sep. 2006; retrieved on Feb. 25, 2013 from <http://www.scielo.br/scielo.php?script—sci_arttext&pid=S0004-282X2006000400012>.

Trabold, B., et al.; "*Synthetic inotropes inhibit the expression of adhesion molecules and augment the expression of L-selectin in polymorphonuclear neutrophils*;" Resuscitation, vol. 74, No. 2; pp. 352-356; dated Aug. 2007.

Tsukahara, H., et al.; "*Oxidative stress in childhood meningitis: measurement of 8hydroxy-2'-deoxyguanosine concentration in cerebrospinal fluid*;" Redox Report, vol. 5, No. 5; pp. 295-298; dated Jul. 2000.

Working Party of the British Society for Antimicrobial Chemotherapy; "*The management of neurosurgical patients with postoperative bacterial or aseptic meningitis or external ventricular drain-associated ventriculitis*;" Infection in Neurosurgery; Br JNeurosurg, vol. 14, No. 1; pp. 7-12; dated Feb. 2000; retrieved on Feb. 25, 2013 from <www.cwmicrobiology.nhs.uk/NeuroPDFs/EVD_and_meningitis.pdf>.

Zarrouk, V., et al.; "*Evaluation of the management of postoperative aseptic meningitis*;" Clin Infect Dis, vol. 44, No. 12; pp. 1555-1559; dated Jun. 2007; retrieved on Feb. 25, 2013 from <http://cid.oxfordjournals.org/content/44/12/1555.full.pdf+html>.

Zeger, S.L., et al.; "Longitudinal data analysis for discrete and continuous outcomes;" Biometrics, vol. 42, No. 1; pp. 121-130; dated Mar. 1986; retrieved on Feb. 25, 2013 from <www.jstor.org/stable/2531248>.

\* cited by examiner

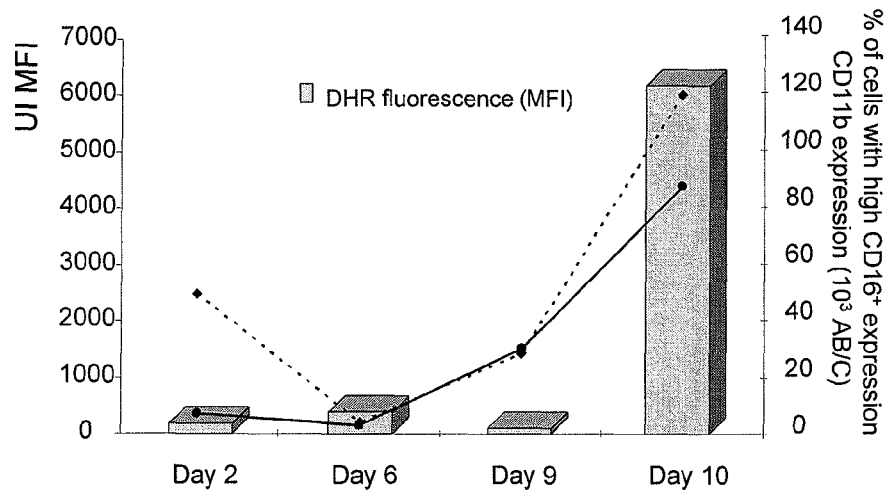
Figure 7
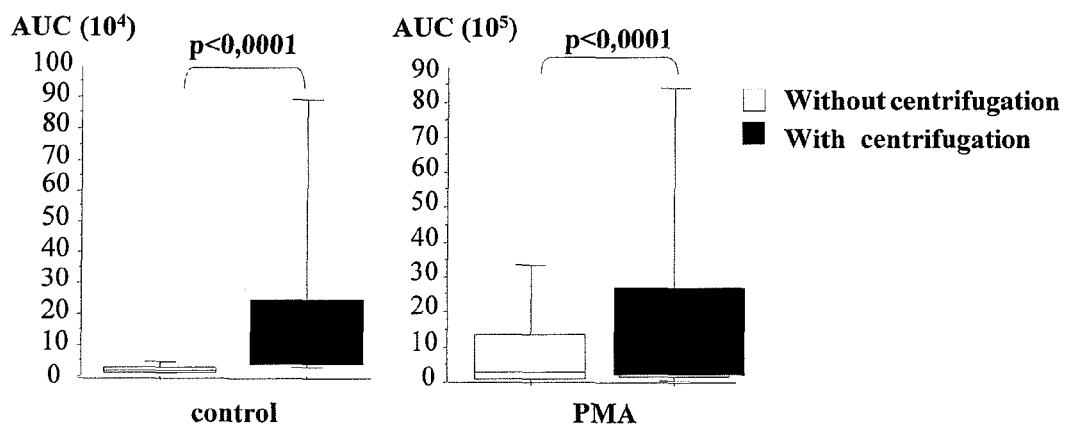
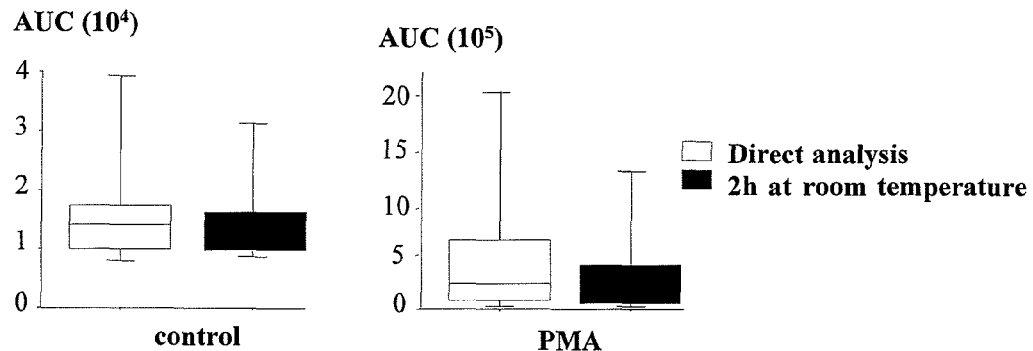
Figure 8A-B

DIAGNOSIS OF BACTERIAL MENINGITIS BASED ON THE MEASURE OF ROS PRODUCTION IN A SAMPLE OF CEREBROSPINAL FLUID

FIELD

The present invention relates to the field of diagnosis. In particular, the present invention provides methods and kits to know, in less than one hour, if a patient suspected to have a meningitis or an infection of the ascites, pericardium, pleura, urinary tract or synovia indeed has a bacterial infection.

BACKGROUND

The diagnosis of central nervous system infection remains challenging for physicians because (i) community meningitis is still associated with high mortality rate and morbidity, and (ii) the diagnosis in context of intracranial injury and procedure is very difficult.

For the community meningitis, positive diagnosis is an emergency for starting antibiotherapy, especially in bacterial meningitis as *Streptococcus pneumoniae, Neisseria meningitis* or *Hemophilus influenzae*.

For post injury or postoperative meningitis, clinical outcome is generally favourable, and treatment less emergent. Nevertheless, the clinicians have to differentiate infected from aseptic meningitis (Ross et al., 1988) and the difficulties of diagnosis result in the wide use of large spectrum antibiotics before confirmation of infection or not (Working Party of the British Society for Antimicrobial Chemotherapy, 2000). This favours iatrogenic over-selection of resistant organisms (Zarrouk et al., 2007). Micro-organisms implicated in such nosocomial meningitis relate to the large spectrum of bacteria in the patient's colonisation, especially *Staphylococcus*, (*aureus* or coagulase negative), enterobacteria and *Pseudomonas*.

In both contexts, a rapid, specific, sensitive test for diagnosis of CSF infection is needed for helping therapeutic decision-making in clinical practice because:

1) symptoms and clinical presentation could be mild and non specific (fever, confusion, leukocytosis), sometimes masked by corticoids or therapeutic hypothermia (trauma or neurosurgical context), 2) classical meningitis criteria of cerebro-spinal fluid (CSF) analysis (pleiocytosis with high proportion of polymorphonuclear neutrophils (PMNs), low glucose and high protein level) are difficult to interpret if recent bleeding or recent surgical procedure, 3) direct bacteriological examination results may be negative especially when on-going antibiotic therapy for other infection is continued (Druel et al., 1996).

PMNs in cerebrospinal fluid (CSF) are the first line of defence in innate immune response to bacterial infection, and their phenotype may constitute the hallmark of infection (Tavares et al., 2006). One component of the killing system of PMNs is the radical oxygen species (ROS) production, also called respiratory burst (Segal, 2005). In this function, the NADPH oxidase plays a pivotal role by pumping superoxide ion ($O_2.$) into phagocytic vacuoles. Superoxide production and its reaction products are collectively referred to as ROS (for radical oxygen species or reactive oxygen species, since both terms are used in the literature). They can be detected and measured by luminescence, fluorescence or colorimetry after oxidation of reactive components (Freitas et al., 2009).

SUMMARY

In this context, the inventors have investigated the possibility to use ROS production by PMNs in CSF as a hallmark of meningitis. The results presented in the experimental part below demonstrate that ROS production in CSF can be used to detect a leukocytosis in CSF and to discriminate bacterial meningitis from aseptic CSF. These results can be transposed to similar situations of infections of biological fluids such as ascitic fluid, pericardial fluid, pleural fluid, urine and synovial fluid, as well as to broncho-alveolar lavage, in which ROS production can be indicative of an activation of phagocytes, in particular of polymorphonuclear neutrophils (PMNs). Importantly, activated neutrophils also produce reactive nitrogen species (RNS), which can also be detected for diagnosing a bacterial infection in certain fluids, especially in urine.

A first aspect of the present invention is hence a method for in vitro diagnosing a leukocytosis and/or a bacterial infection in a biological fluid selected in the group consisting of cerebrospinal fluid, ascitic fluid, pericardial fluid, pleural fluid, urine and synovial fluid, comprising a step of measuring the production of reactive oxygen species (ROS) and/or reactive nitrogen species (RNS), in a sample of said fluid collected from a patient suspected to have an infection. According to this method, a ROS and/or RNS production above a predetermined threshold is indicative of leukocytosis and/or bacterial infection. The inventors have demonstrated that the conditions in which the ROS and/or RNS production is measured can give results which are particularly informative either for detecting leukocytosis or for detecting the presence of a bacterial infection. Indeed, in the above method, the level of ROS produced by the polymorphonuclear neutrophils (PMNs) present in the sample of biological fluid can be measured either in absence of stimulation of said PMNs, or after stimulation of said PMNs by a direct or indirect agonist of NADPH oxidase. As a functional test, both conditions (unstimulated and stimulated) can be performed and the obtained results can be compared. Examples of agonists of NADPH oxidase which can be used when performing the method of the invention are PMA (phorbol 12-meristate 13-acetate), LPS (lipopolysaccharides), fMLP (N-formyl-methionyl-leucyl-phenylalanine) or opsonised yeast particles (Freitas et al., 2009). PMA, which is usually considered as the most direct agonist of NADPH oxidase, acts via the protein kinase C. As shown in the experimental part below, ROS production above a determined threshold in stimulated conditions is indicative of leukocytosis, whereas the spontaneous ROS production (in absence of stimulation) is more informative for detecting a bacterial infection.

Depending on the situation, an appropriate threshold can be determined by the skilled artisan by measuring ROS and/or RNS production in a representative cohort (for example, a cohort of at least 10 patients having the considered infection and at least 10 uninfected patients). Examples of factors which can impact on the threshold are (i) the biological fluid which is tested (CSF, ascitic fluid etc.), (ii) the clinical context, (iii) the treatment of the sample between collection and the test, (iv) the method for measuring the production of ROS and/or RNS, and (v) the level of sensitivity vs. specificity which is needed. The clinical context can be of importance for determining a relevant threshold. For example, in the case of meningitis, the threshold will not be the same in case of suspicion of community meningitidis and in case of possible nosocomial meningitidis. Indeed, in the first case (i.e., in absence of brain trauma of any kind), a ROS production, even very low, is indicative of a meningitis since the CSF is acellular in normal conditions, whereas after a brain trauma or surgery, white blood cells are present in the CSF, resulting in a "background noise" which necessitates the determination of a threshold to distinguish this noise from ROS production due to an infection. The importance of the parameters (iii), (iv)

and (v) is illustrated by the examples, in which two different protocols have been studied for preparing the samples and measuring spontaneous ROS production. The first protocol (Example 1) comprises a centrifugation step which is omitted in the second one (Examples 2, 3 and 6). Using the same luminometric technique for measuring ROS production, the threshold with the first protocol is nearly ten-fold more superior to that with the second one (around $10^6$ RLU in Example 1, vs. $7.5 \times 10^5$ in Example 6). Of course, the threshold in activated condition (in presence of an agonist of NADPH oxidase) is superior to that in absence of stimulation.

Since the above method measures the activity of living cells, the test is preferably performed shortly after collection of the sample. The measure of ROS production by the PMNs present in the sample of biological fluid in hence preferably performed at most eight hours after sample collection, more preferably less than four hours after sample collection. The sample must not be frozen before testing.

In a particular embodiment, ROS and/or RNS production is measured in a sample of cerebrospinal fluid; a ROS and/or RNS production above a predetermined threshold, especially in spontaneous condition (in absence of stimulation) is then indicative of bacterial meningitis. As mentioned above, the threshold will be determined by the skilled artisan depending on several criteria, such as the technology used to measure ROS and/or RNS production etc. In the particular case of meningitis, the threshold will be preferentially chosen to avoid false negative results, i.e., to obtain a good sensitivity.

The method will be advantageously performed in CSF in different clinical contexts:
  suspicion of community meningitis
  invasive intracranial procedures: ventriculostomy catheter (or external ventricular drainage (EVD)), catheters for intracranial pressure measurements, endovascular device (coils, prosthesis), recent neurosurgery
  brain trauma or traumatic brain injury (TBI)
  invasive intradural procedure: external lumbar drainage.

Risk factors of infection are: haemorrhage, duration of catheterization, emergency procedure and CSF leak (Mayhall et al., 1984).

According to another particular embodiment of the method described above, ROS production is measured in a sample of 250 µl of cerebrospinal fluid, incubated 10 minutes in the dark with 50 µM of luminol in a final volume of 1 ml. In this case, the results can be expressed, for example, as area under the curve (AUC) of luminescence over 20 minutes (of course, the volumes, luminol concentration and duration of incubations can be adapted by the skilled artisan). In this case, illustrated in the examples below, a threshold of $6.10^5$ to $6.10^6$ RLU in absence of stimulation of PMNs can be used (depending on the treatment of the sample before the test), which means that a ROS production leading to a result above this value is indicative of bacterial meningitis.

Of course, the skilled artisan can chose any method for ROS and/or RNS detection. A review of such methods available to date is described by Freitas et al. (2009) and summarized in Example 5 below. Any method described in this article can be used to perform the present invention. As noted by Freitas et al., none of the methods described to date for ROS and/or RNS detection is perfect, and the drawbacks of the probes differ. The skilled artisan will hence chose a detection method depending on the constraints of clinical application. It is to be noted that it is not compulsory, for efficiently performing the invention, to use more than one probe, as recommended by Freitas et al (Freitas et al., 2009).

In another preferred embodiment of the method according to the invention, ROS and/or RNS production is measured by putting a sample of biological fluid in presence of a colorimetric reagent sensitive to said ROS and/or RNS, i.e., a reagent the colour of which changes in presence of ROS and/or RNS. In a particularly preferred embodiment, the colorimetric reagent is on a testing strip.

As already mentioned above, the test according to the present invention can be performed by measuring ROS production in both stimulated and non-stimulated conditions. In this case, a conclusion of absence of infection can be drawn directly if both measures are below their corresponding predetermined thresholds. In a particular embodiment of the invention, if one or both of the measures is above a predetermined threshold, the sample is sent to a laboratory of bacteriology for further analysis (by culture).

The present invention hence also pertains to a method comprising the steps of:
  (i) measuring the level of ROS spontaneously produced by the PMNs present in the sample of biological fluid, and
  (ii) measuring the level of ROS produced by the PMNs present in the sample of biological fluid after stimulation by an agonist of NADPH oxidase,
  wherein:
  a) if the level measured in step (i) is below a first predetermined threshold and the level measured in step (ii) is below a second predetermined threshold, it is concluded that there is no bacterial infection in the biological fluid;
  b) if the level measured in step (i) is above a first predetermined threshold, a bacteriological analysis of the sample is conducted; and
  c) if the level measured in step (ii) is above a second predetermined threshold, a bacteriological analysis of the sample is conducted.

Interestingly, this method leads to an economy of unnecessary analyses, since in case a) unnecessary bacterial analysis are avoided. Importantly, in this case, unnecessary antibiotherapy is also avoided, which is beneficial both to the patient and to the local ecology.

In case b), there is an important probability that an infection is present. According to a particular embodiment of the above method, the clinician will thus give antibiotics to the subject without waiting for the results of the bacteriological cultures.

In case c), the clinician can also initiate the antibiotherapy even if the level of spontaneous ROS production is below the predetermined threshold, but, depending on the context, this decision can also be postponed.

The invention can also be used for in vitro assessing the efficiency of an antibiotic treatment in a patient having a bacterial infection. Indeed, in case of bacterial infection in a biological fluid such as cerebrospinal fluid, ascitic fluid, pleural fluid, urine and synovial fluid, activation of neutrophils leads to a high production of ROS and RNS, which decreases rapidly after the beginning of antibiotherapy, provided this therapy is efficient. Therefore, by performing a follow-up of ROS and/or RNS production in biological samples from the locus of infection, after the beginning of antibiotherapy, the physician will be able to know if the antibiotic is efficient or not (a decrease in ROS production after the beginning of the antibiotic treatment indicates that said treatments is appropriate). As shown in Example 4 below, an efficient antibiotherapy in case of bacterial meningitis leads to a rapid decrease of ROS production (in both activated and spontaneous conditions), since 3 days after antibiotic administration, the production level has decreased to the same level as before the beginning of infection. Two other similar examples are shown in Example 6.

The invention can be used as well for in vitro detecting a treatment failure, especially after a brain trauma or an invasive intracranial or intradural procedure. For doing so, PMNs activation in CSF is monitored by measuring ROS production in at least one or two distinct CSF samples which have been taken after the beginning of said treatment. A persistence of ROS production above a predetermined threshold indicates the failure of treatment, which can be due either to an uncontrolled source of infection (such as a persisting CSF leak, infected material, and abscess etc.), or to a restart of infection due to resistant bacteria. The predetermined threshold considered for this aspect of the invention can be the same as the threshold for detecting the presence of a bacterial infection, but a lower threshold, still above the baseline, can also be used. An example of such a threshold is the value of the $75^{th}$ percentile of the aseptic cohort (which would be, in the case of Example 1, around 100 $10^5$ in control condition and 1500 $10^5$ after stimulation).

Another aspect of the present invention is a diagnostic kit for performing a method as described above, comprising a reagent which can react with ROS and/or RNS, and a notice of use indicating how to interpret the results. In a preferred embodiment, this reagent is a colorimetric reagent. In an even more preferred embodiment, the kit comprises one or several testing strip(s) covered with at least one colorimetric reagent reacting with ROS and/or RNS, and a notice of use indicating the correspondence between the colour of the strip after incubation with a sample of biological fluid and the likelihood of bacterial infection in said fluid. According to a preferred embodiment, the kit also comprises an agonist of NADPH oxidase.

BRIEF DESCRIPTION OF THE DRAWINGS

The present invention will be more fully understood by reading the experimental part which follows, illustrated by the figures.

LEGENDS TO THE FIGURES

Figure 1:
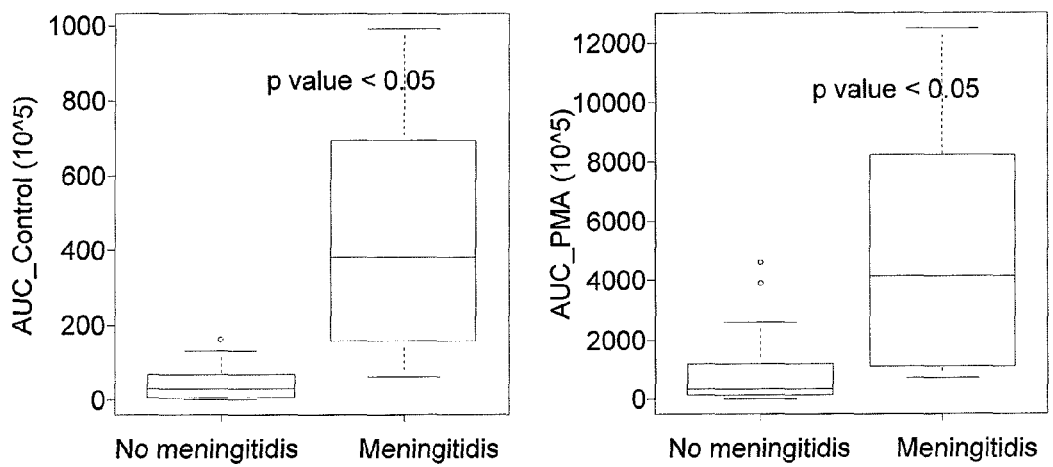

FIG. 1: luminescence of CSF samples in control conditions (on the left) or after stimulation by PMA (on the right) according to meningitis diagnosis.

Figure 2:
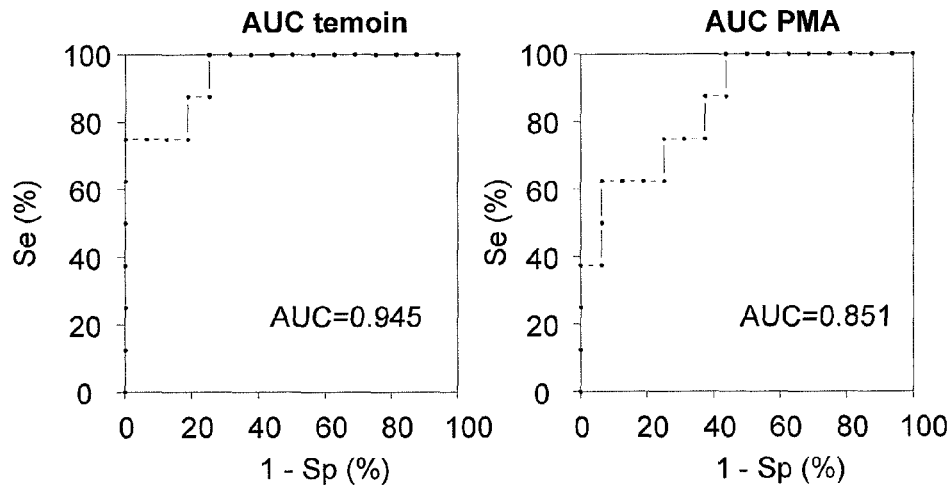

FIG. 2: ROC (Receiving Operator Characteristics) curves representing the specificity (Sp) and sensibility (Ss) according to the chosen threshold, for the tests presented in Example 1.

Figure 3:
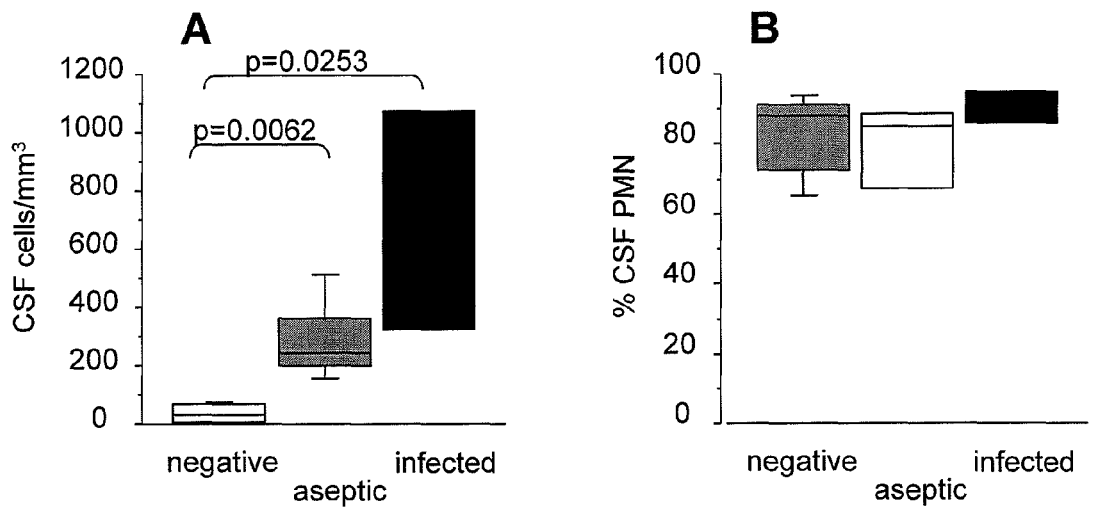

FIG. 3: cell count in CSF (A) and PMN percentage (B) according to the diagnosis of meningitis. Analysis by Mann Whitney tests.

Figure 4:
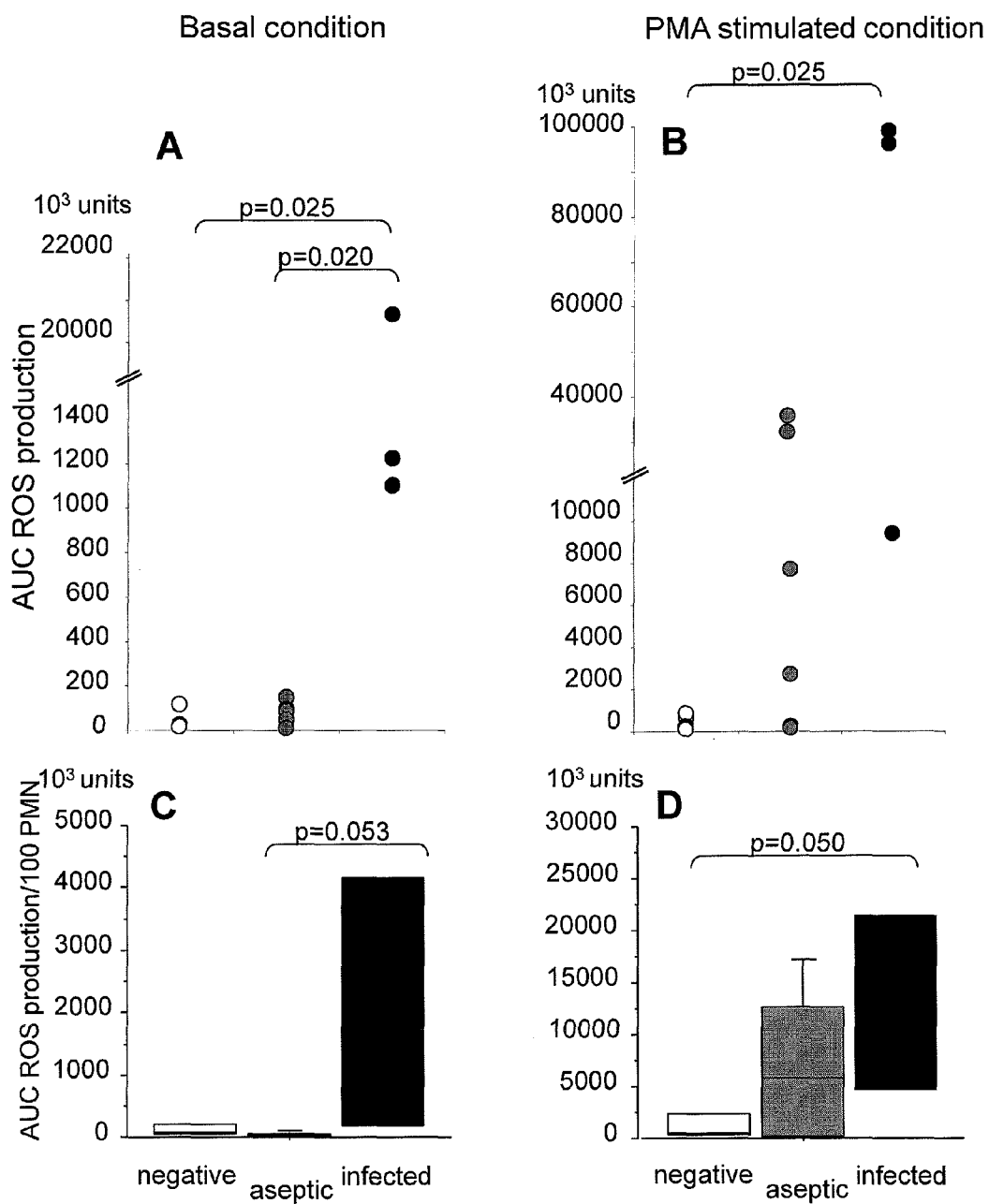

FIG. 4: Quantity of ROS produced by cells from 250 µL of CSF in basal condition (A) and after stimulation by PMA (B) according to the diagnosis of meningitis. Same measures reported to 100 PMN in basal condition (C) and after PMA stimulation (D). Mann Whitney tests.

Figure 5:
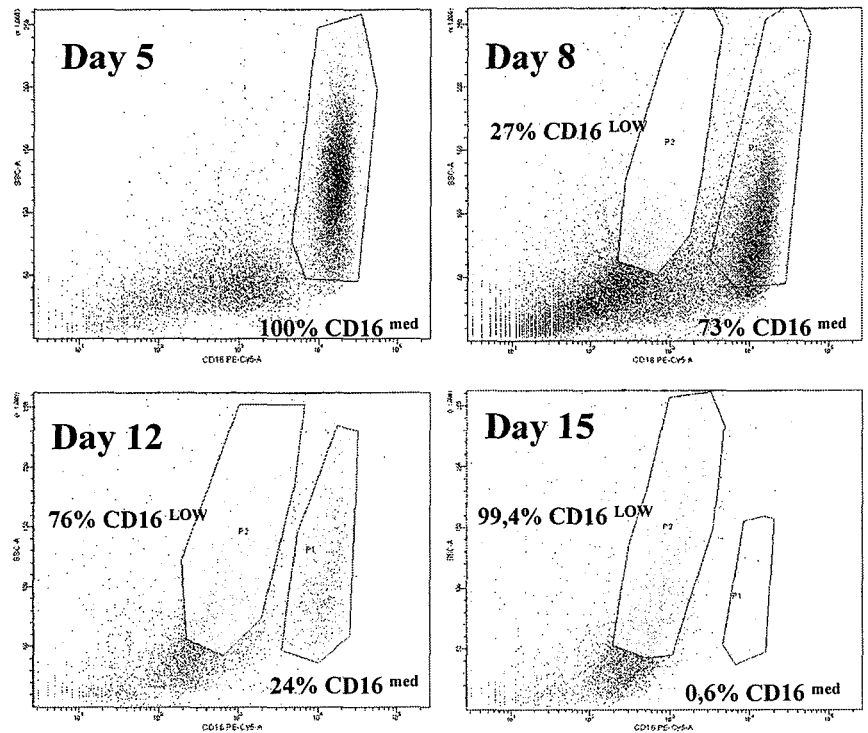

FIG. 5: an example of CD16 expression on PMNs overtime during the EVD at day 5, day 8, day 12 and day 15.

Figure 6:
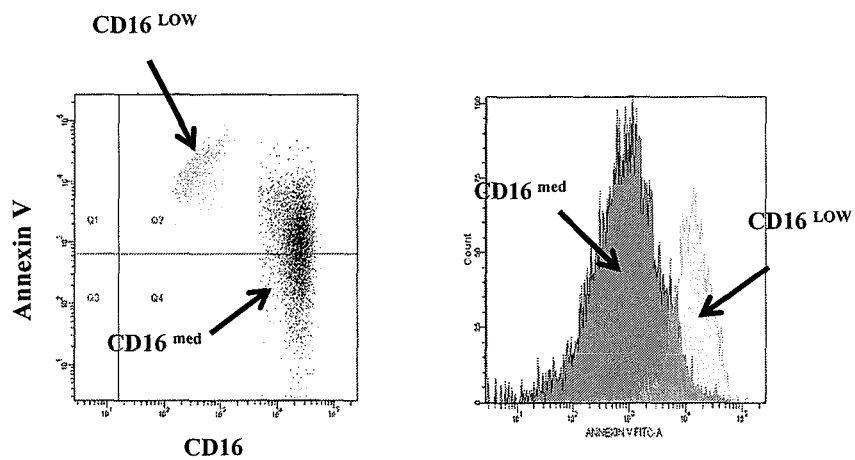

FIG. 6: annexin V expression on $CD16^{med}$ and $CD16^{low}$ PMNs in CSF.

FIG. 7: follow up of CD16, CD11b expression and DHR fluorescence (flowcytometry) by CSF PMNs in patient with ventriculo-meningitis at day 10. DHR intensity are gray bars, CD11b expression full line, % of cells with $CD16^{med}$ expression dotted line.

FIG. 8: ROS production measured in CSF (A) after CSF centrifugation or not, (B) directly or after 2 hours at room temperature, (C) directly or after 2 hours at 4° C.

Figure 9:
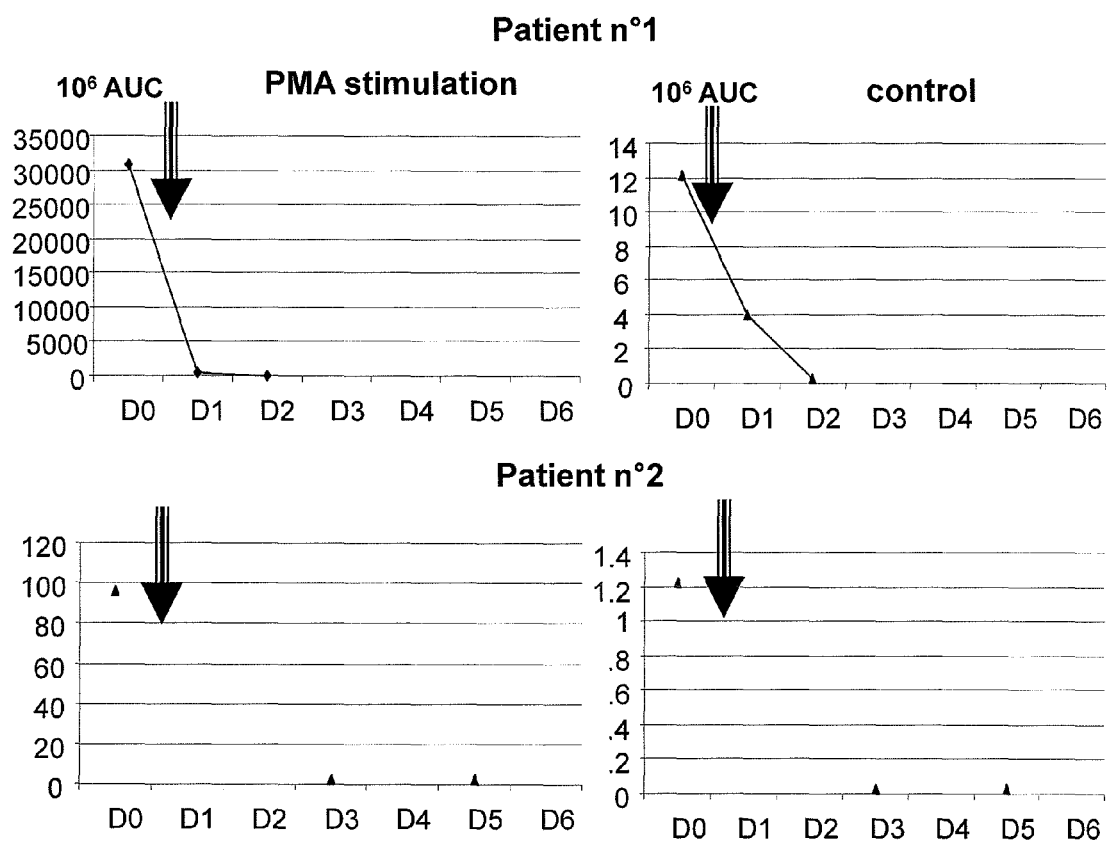

FIG. 9: kinetics of measures by luminometry in CSF before and after introduction of antibiotics (arrow) in two patients. Measures in control condition and with PMA stimulation are presented and expressed as area under the curve (AUC).

Figure 10:
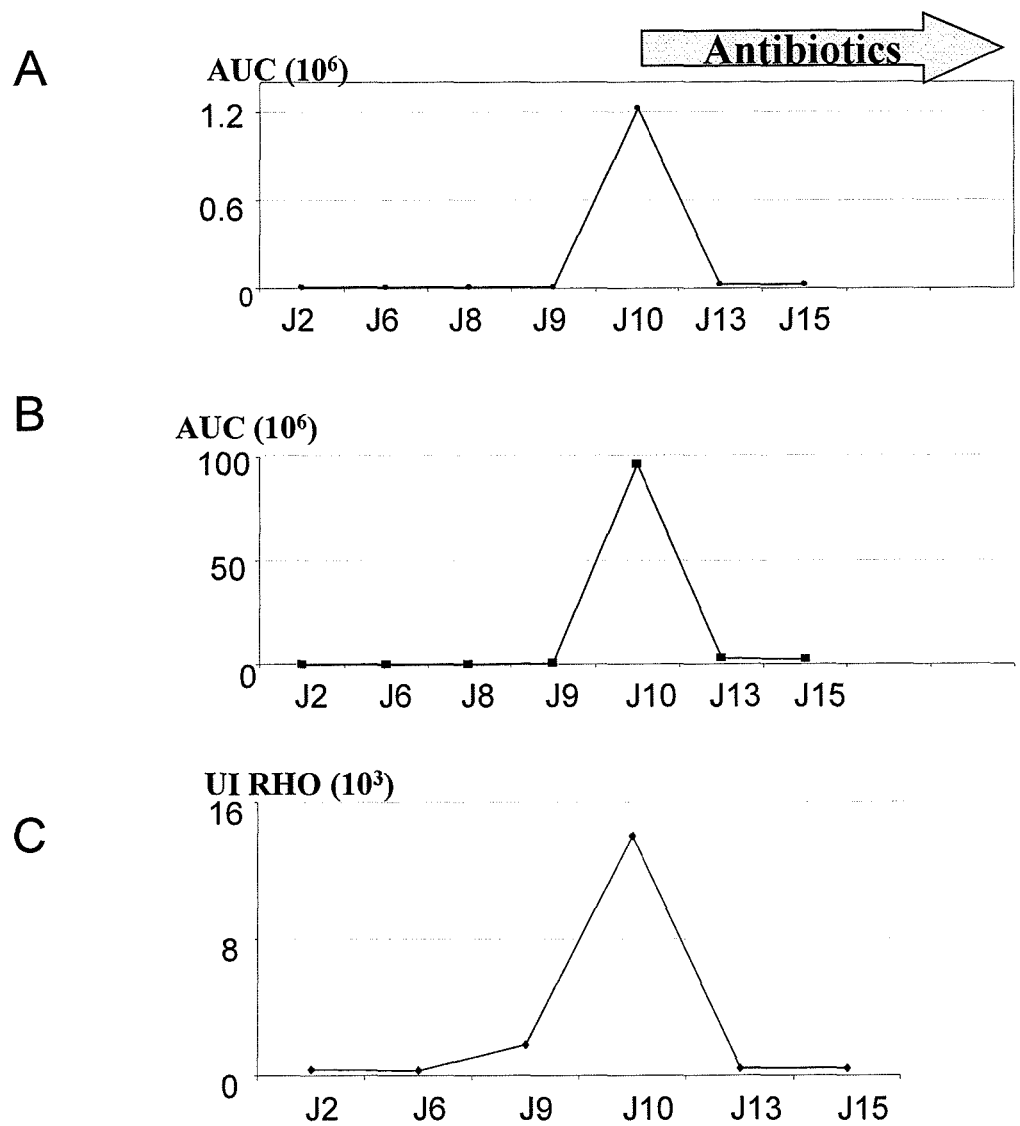

FIG. 10: kinetics in control (A) or stimulation (B) conditions and by flowcytometry (C) in one patient.

Figure 11:
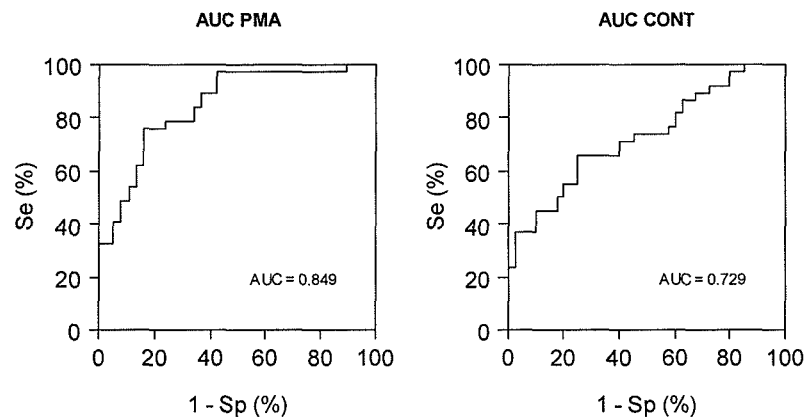

FIG. 11: The Receiver Operating Characteristics (ROC) of AUC PMA (stimulated condition) and AUC CONT (control condition) in association with CSF leukocytosis as in the septic and aseptic meningitis. AUC=Area under curve; Se=sensitivity; Sp=specificity.

Figure 12:
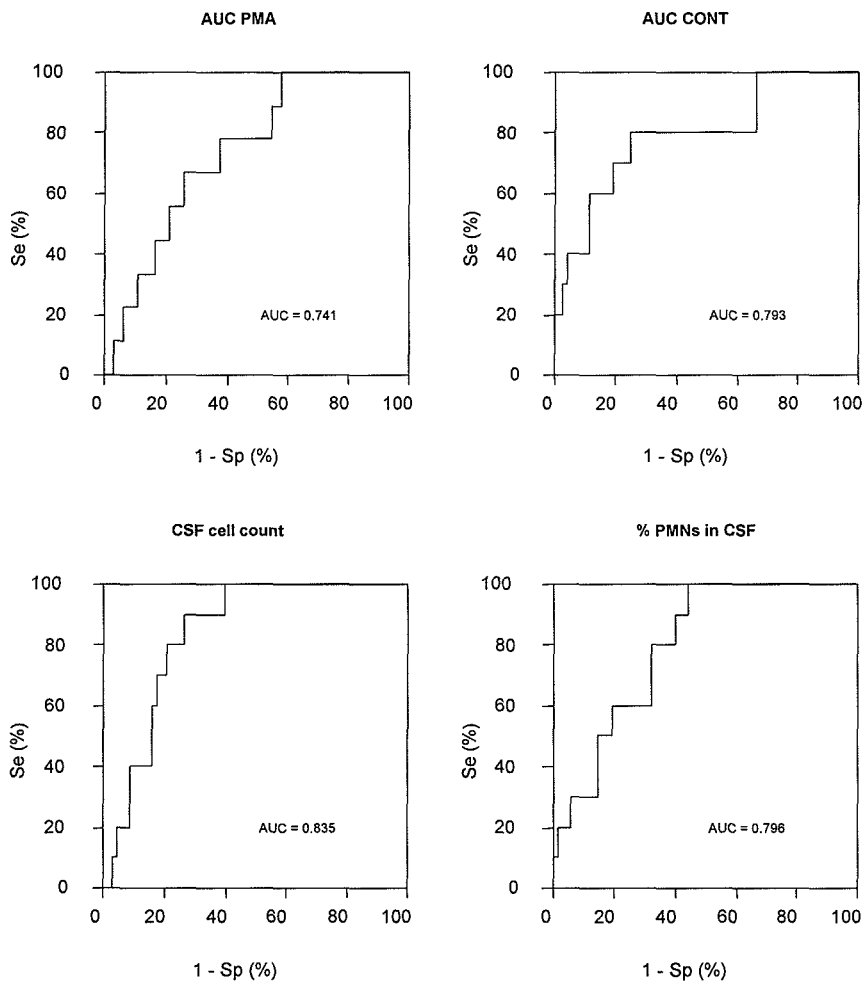

FIG. 12: The ROC curves of AUC PMA (stimulated condition), AUC CONT (control condition), CSF cell count and % PMNs in CSF, for prediction of bacterial presence. Se=sensitivity; Sp=specificity.

Figure 13:
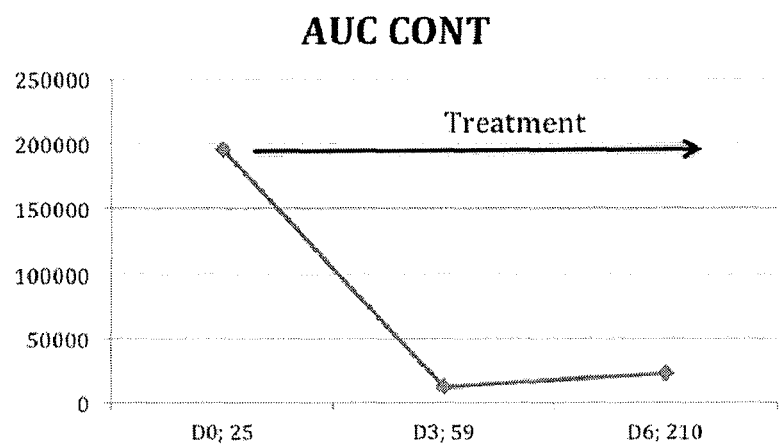

FIG. 13: Evolution of ROS production in CSF for a patient with septic meningitis at day 0 (D0 is the day of diagnosis). Antibiotic treatment was initiated after the first sample. The CSF cell count is presented next to the days in question.

Figure 14:
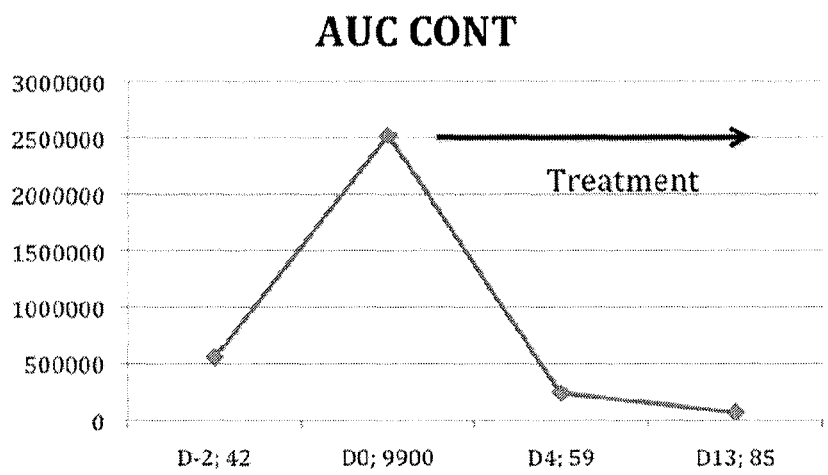

FIG. 14: Evolution of ROS production for a patient who was started on treatment after D0 but whose cultures remained negative, throughout these days. The CSF cell count is presented next to the days in question.

EXAMPLES

Example 1

Case Control Study

Materials and Methods

Inclusion criteria: patients with suspicion of meningitis (fever above 38° C.), in postoperative context, with external ventricular device (EVD), or brain trauma. Constitutive inclusions along 2008.

Statistical analysis: cases and controls were matched for initial pathology (trauma, scheduled surgery, emergent surgery, subarachnoid haemorrhage), the presence of the EVD, the delay from the initial pathology.

Measure of ROS Production by PMNs in CSF 1 ml of CSF was diluted in 4 ml of Hanks' Balanced Salt Solution (HBSS) at 4° C., then centrifugated (370 g, 10 min) and cell culot resuspended in 160 µl HBSS. Control and stimulation conditions were tested in duplicate, 40 µl per condition. Cells are incubated for 10 min in 1 ml final volume of HBSS with luminol (50 µM) at 37° C. in the dark.

At the end of incubation, as a functional test in stimulation condition, Phorbol 12-myriaste 13-acetate (PMA) was added for a final concentration of $10^{-7}$M just before luminometry. Immediate analysis was done in luminometer (Auto Lumat Plus LB 953), one second every 60 seconds over a 20 minutes period.

Results

Eight patients with bacterial meningitis (positive bacteriological analysis of CSF) were compared with 16 patients with negative CSF analysis.

The spontaneous luminescence of CSF samples, as well as the luminescence after stimulation with PMA, are shown in FIG. 1, and the corresponding ROC curves are shown in FIG. 2.

Tables 1 and 2 below show the derived sensitivity and specificity in both conditions.

TABLE 1 derived sensitivity (Se) and specificity (Spe) in control condition for meningitis diagnosis.

| Thresholds | 1 − Spe | Se |
|---|---|---|
| 1750000 | 62.5 | 100 |
| 2730000 | 56.25 | 100 |
| 2960000 | 50 | 100 |
| 3050000 | 43.75 | 100 |
| 5030000 | 37.5 | 100 |
| 5760000 | 31.25 | 100 |
| 6040000 | 25 | 100 |
| 7330000 | 25 | 87.5 |
| 11200000 | 18.75 | 87.5 |
| 12300000 | 18.75 | 75 |
| 1.3e+07 | 12.5 | 75 |
| 1.6e+07 | 6.25 | 75 |
| 20100000 | 0 | 75 |
| 36200000 | 0 | 62.5 |

TABLE 2 derived sensitivity (Se) and specificity (Spe) in stimulated condition for meningitis diagnosis.

| Thresholds | 1 − Spe | Se |
|---|---|---|
| 18800000 | 62.5 | 100 |
| 31300000 | 56.25 | 100 |
| 34300000 | 50 | 100 |
| 70500000 | 43.75 | 100 |
| 85700000 | 43.75 | 87.5 |
| 98900000 | 37.5 | 87.5 |
| 1.1e+08 | 37.5 | 75 |
| 1.12e+08 | 31.25 | 75 |
| 1.22e+08 | 25 | 75 |
| 1.24e+08 | 25 | 62.5 |
| 2.59e+08 | 18.75 | 62.5 |

Interpretation: in clinical practice, the physician will chose a threshold related to high sensitivity leading to the administration of antibiotics to patients with high risk of meningitis. Such a test will avoid antibiotic administration to patients with very low risk of meningitis.

Example 2

Evidence of Radical Oxygen Species Production by Neutrophils in Infected Cerebrospinal Fluid Related to External Ventricular Drain Materials and Methods
Patients and Methods This study was approved by the Institutional Review Board (IRB 00006477; Jun. 28, 2008). Patients with ventricular haemorrhage requiring external ventricular drainage admitted from February to September 2009 in the ICU of Lariboisière Hospital (Paris, France) were selected. All patients received prophylactic antibiotics for ventriculostomy and catheter insertion according to the institution protocol. Physician in charge was not aware of investigations and patient management was independent to the findings.

Definitions of Ventriculo-Meningitis 1) a meningitis was considered to be aseptic if a CSF sample contained >100 leukocytes/mm$^3$ and direct examination and culture results were negative after 72 h; 2) a meningitis was considered to be septic ("infected" group) if CSF was positive on direct examination or by culture and as CSF sample contained >100 leukocytes/mm$^3$; 3) a contamination was considered if direct examination and culture results of CSF were positive without alterations of CSF composition; 4) CSF was considered negative if leukocyte count <100 leukocytes/mm$^3$ and direct examination and cultures were negative (Forgacs et al., 2001; Zarrouk et al., 2007).

Clinical and Biological Data Collection

For each patient, the following data were collected: demographic characteristics, indication for external ventricular drainage, clinical manifestations of infection and biological findings (CSF cytology, protein and glucose levels, and blood sample findings), treatment regimen at the time of sampling and outcome. Other concomitant site of infection and antibiotic regimen were also collected, if any.

Measurements of ROS Production by Luminometry

250 µl of CSF was diluted in Hanks' Balanced Salt Solutions (HBSS, Invitrogen, Cergy-Pontoise, France) to a final volume of 1 ml and incubated with luminol (50 µM, Sigma, Saint Quentin Fallavier, France) for 10 min at 37° C. in the dark. As a functional test, a control was compared to a stimulated condition with $10^{-7}$M of PMA (phorbol 12-myristate 13-acétate, Sigma), each condition in duplicate. The light produced by luminol in presence of ROS was analysed immediately in a luminometer (AutoLumat Plus LB 953, Berthold Technologies, Bad Wildbad, Germany) over a 20-min period. The signal was recorded during one second, every 60 sec and expressed as Relative Light Units (RLU). Results were expressed as area under the curve (AUC) of luminescence over the 20 min.

Characterisation of PMN by Flow Cytometry:

After centrifugation (200 g, 10 min, room temperature), CSF cells were resuspended in 50 µl of CSF and incubated in presence of specific antibodies for 30 min, in the dark and at room temperature. For PMNs selection in flow cytometry analysis, we used anti-CD16-Phycoerythrine-Cyanine 5 (PC5) antibody (Beckman Coulter, Marseille, France), and phenotype was assessed using anti-CD11b-Phycoérythrine (PE) or anti-CD62L-PE (BD Bioscience, San Jose, Calif. USA). Unspecific binding of antibodies to cells Fc receptors was assessed with a control isotype. Red cells were eliminated after incubation with lysing solution (BD FACS Lysing Solution, BD Bioscience) for 10 min in the dark, at room temperature, and washing with phosphate buffer saline (PBS, Gibco Invitrogen, Grand Island, N.Y., USA). After centrifugation (300 g, 10 min, room temperature), cell pellet was suspended in PBS with 1% paraformaldehyde (PFA, Sigma) and stored at 4° C., in the dark, until analysis by cytometer (FacsCanto, and FacsDiva software, Becton Dickinson).

Apoptosis Analysis

After incubation with anti-CD16-PC5 and red cells lysis, some of the samples were used to quantitate apoptosis by annexin-V measurements with flow cytometry (apoptosis detection kit, Sigma). Technical procedure was done according to manufacturer recommendations.

Measurements of ROS Production by Flow Cytometry:

After centrifugation (200 g, 10 min, room temperature), CSF cells were resuspended in 50 µl of CSF and incubated in presence of dihydro-rhodamine 123 (DHR123, 7.5 $10^{-6}$ M, Sigma) and anti CD16-PC5 for 30 min in the dark and at 37° C. Red cells were eliminated after incubation with lysing solution (BD FACS Lysing Solution, BD Bioscience) for 10 min in the dark, at room temperature, and washing with PBS. After centrifugation (500 g, 10 min, 4° C.), cell pellet was suspended in PBS for immediate analysis by flowcytometer.

Measures obtained in blood PMNs from healthy volunteers (HV) with the same protocol (50 µl) were considered as reference values for PMNs at rest.

Statistical Analysis:

Quantitative variables were expressed as median (interquartile range, IQR). Analysis has been performed with non parametric Mann-Whitney and Kruskal Wallis tests.

Results

Fourteen patients required EVD because of intraventricular haemorrhage: 8 subarachnoid haemorrhage by aneurysm rupture, 2 parenchymal haematoma, 2 operated tumors of posterior fossa, 1 severe brain trauma and 1 arteriovenous malformation. Six patients met criteria of aseptic ventriculo-meningitis, 3 infected ventriculo-meningitis and 5 febrile patients (over 38° C.) without major alteration of CSF cytology or infection were considered as "negative" for meningitis.

The micro-organisms found in the 3 infected CSF were *Pseudomonas aeruginosa* and *Staphylococcus epidermidis* and *Corynebacterium*. Table 3 summarizes the clinical and biological characteristics of patients. No patients died in the infected group; the 2 deaths occurred in the "negative" group in relation with the severity of the intracranial vascular pathology.

TABLE 3 clinical and biological characteristics of the 14 patients. Results are expressed in median (InterQuartile Range). Intergroup comparison by Kruskal-Wallis test.

|  | negative, n = 5 | aseptic, n = 6 | infected, n = 3 | p |
|---|---|---|---|---|
| Age (years) | 56 (8) | 57 (27) | 36 (10) |  |
| Drainage time (days) | 5 (4) | 7 (2) | 13 (19) | 0.049 |
| Temperature (° C.) | 38.9 (2.2) | 39.3 (0.8) | 40.6 (0.8) |  |
| Blood leukocytes (109/l) | 10.6 (9.4) | 12.7 (7.8) | 19.1 (8.6) |  |
| CSF cell count (/mm3) | 34 (64) | 245 (160) | 460 (750) | 0.007 |
| CSF % PMN | 85 (22) | 88 (19) | 94 (9) |  |
| CSF glucose (mmol/l) | 3.8 (1.3) | 3.9 (0.9) | 4.0 (4.1) |  |
| CSF proteins (g/l) | 0.56 (0.17) | 0.49 (0.30) | 1.21 (0.50) | 0.032 |

According to the definition, cell count in CSF was higher in "infected" and "aseptic" groups compared to "negative" group and the highest count was recorded in the infected group (FIG. 3A, Table 3). No difference in percentage of PMNs was reported between groups (FIG. 3B, Table 3).

Global ROS Production in Infected and Aseptic CSF

At the basal state, ROS production was significantly higher in infected group than in aseptic group or "negative" group (FIG. 4A). After PMA stimulation (FIG. 4B), a higher ROS production was observed in CSF from infected group compared to "negative" group, but not compared to the aseptic group. When ROS production values were normalised to PMNs number (per 100 PMNs, FIGS. 4C and 4D)), the same trends were obtained, but with smaller differences.

PMN Phenotype in CSF along EVD

Six patients were repeatedly sampled for CSF PMNs characterization along EVD, one of them presented an infection at day 10 (Table 4). The flow cytometry analysis showed clearly two distinct populations of PMNs according to CD16 expression (FIG. 5), both with low fluorescence intensity (5081 (3181) and 382 (270) UI MFI respectively called $CD16^{med}$ and $CD16^{low}$ cells) compared to HV blood PMNs (12530 (8325) UI MFI, $CD16^{high}$ cells). The proportion of $CD16^{med}$ cells decreased over time (FIG. 5). Analysis of CD11b expression (AB/C) and percentage of CD62L positive (% CD62L+) cell were similar to blood PMN values from HV over the couple of days, decreasing with later times of EVD (Table 4). ROS production evaluated by DHR 123 fluorescence showed similar production than in HV blood PMNs. CSF PMNs showed an increased annexin V expression at cell surface especially in the $CD16^{low}$ population (FIG. 6).

Conversely, the infected CSF was characterized by an increased number of $CD16^{med}$ cells, and high CD11b expression and DHR fluorescence (Table 4, FIG. 7).

TABLE 4 inflammatory phenotype of PMNs in blood from HV and over CSF follow up in patient. Results are expressed in median (interquartile range).

|  | Blood HV n = 19 | Aseptic CSF follow-up along drainage period | | | | Infected CSF |
|---|---|---|---|---|---|---|
|  |  | day 1-4 n = 6 | day 5-9 n = 4 | day 10-15 n = 4 | after day 16 n = 1 | day 10 n = 1 |
| $CD16^{med}$ + cells (%) | 100 ($CD16^{high}$) | 72 (32) | 89 (51) | 30 (52) | 0 | 87 |
| CD11b (AB/C) | 47900 (59768) | 43800 (19900) | 37300 (20500) | 33600 (4275) | 11700 | 119100 |
| CD62L + cells (%) | 12 (15) | 17 (42) | 27 (36) | 5 (5)* | 3 | 3 |
| DHR 123 (UI) | 251 (738) | 200 (30) | 290 (153) | 159 (215) | 307 | 6195 |

*p < 0.05 vs HV, Mann Whithney test.

Discussion

This study illustrates the level of ROS production by CSF PMNs as a hallmark of infection of CSF in patients with EVD. CSF samples related to on-going infection exhibited a higher production of ROS compared to aseptic CSF in a context of febrile intraventricular haemorrhage. In aseptic CSF, PMNs presented low levels of CD16, similar CD111b and CD62L expression compared to blood PMNs from HV. CD16 and CD11b were re-expressed on PMNs from infected CSF. The measurement of ROS production in CSF may discriminate infected from aseptic CSF.

EVD is classical in the management of intraventricular haemorrhage related to spontaneous bleeding or postoperatively but complicated by infection in 5 to 20% of cases (Bota et al., 2005; Hader and Steinbok, 2000; Holloway et al., 1996). Usually, infection of ventricular CSF (ventriculitis) is coming from the contaminated catheter. In case of bloody CSF, the sampling and analysis (pleiocytosis, glucose and proteins) of ventricular CSF does not permit the rapid diagnosis with certitude before microbiological results. Highest cell count has been measured, especially for PMNs, in case of infection but with a large overlap with aseptic samples, preventing the determination of a clear threshold for accurate discrimination. Nevertheless, in case of infection, as the first line of innate immunity, newly recruited PMNs may present phenotype specific characteristics related to infection. Among these phenotypic characteristics, the inventors studied ROS production, expression of adhesion and activation markers that are rapid to analyse.

A higher production of ROS was measured associated with CSF infection compared to aseptic CSF, spontaneously and after stimulation by PMA. Higher spontaneous production might not be only related to the higher cell count since the ROS production reported to cell was more elevated in infected condition. ROS production might be related to mitochondria production especially in a context of apoptotic evolution (Fay et al., 2006; Li and Trush, 1998; Lundqvist-Gustafsson and Bengtsson, 1999; Serhan and Savill, 2005), but the inventors observed that at least a part of the cells were still responsive to PMA stimulation, as viable cells would. The main source of ROS may be the activation of NADPH oxidase system as supported by the response to PMA stimulation (Li and Trush, 1998; Piccoli et al., 2005). This hypothesis was consistent with the septic context and recruitment of reactive phagocytes, that could even imply the upregulation of enzyme at the transcriptional level (Cassatella et al., 1990).

PMNs in aseptic CSF did not present classical markers of activation but instead showed expression of membrane CD11b or CD62L close to those measured on blood "resting" PMNs, suggesting that no particular activation of rolling, adhesion and diapedesis functions was present. The natural evolution of PMNs dropped in CSF seemed to be apoptosis, as suggested by their membrane expression of annexin V (Serhan and Savill, 2005). Interestingly, in the infected case, the higher level of CD16 expression, likely related to low apoptosis induction, and ROS production suggested the renewal of leucocytes in infected focus. On these PMNs, CD11b was highly expressed and CD62L low on PMNs in the infected context according to the activated phenotype (Trabold et al., 2007).

The inventors measured ROS production by two different methods: 1) intracellular hydrogen peroxide ($H_2O_2$) spontaneous production reacting with DHR by fluorescence and 2) intra- and extracellular global ROS production (superoxide anion in majority) reacting with luminol by luminescence (Freitas et al., 2009). They obtained concordant information with both methods.

With the objective of testing for infection diagnosis, the measurement of spontaneous ROS production by CSF cells seemed to give a better signal than PMA stimulated condition, since no overlap was observed between aseptic and infected samples. This has to be confirmed in a large-scale study. Analysis by luminescence constituted a simpler procedure than DHR fluorescence, more suitable for rapid bedside diagnosis in clinical practice. Such a test would limit the extensive use of large spectrum antibiotics for at least 48 hours, and sometimes the invasive procedures (as replacement of EVD).

This test of ROS production as a hallmark of on-going CSF infection has to be tested and extended to other postoperative and post-injury meningitis. The test could be adapted for community meningitis associated with sufficient recruitment of PMNs in the CNS.

Example 3

Simplified Protocols for Measuring ROS Production by Luminometry

The impact of dilution in HBSS and centrifugation (as described in Example 1) was assessed by comparison with a simplified protocol (as described in Example 2): 64 samples from 11 patients have been analysed at different times over the EVD period. ROS measurements were lower in simplified protocol than after centrifugation: respectively AUC at 16,101 (9,835-35,358) versus 76,336 (41,222-277,007) without PMA, $p<0.0001$ and at 315,592 (90,668-1,504,078) versus 683,190 (169,492-3,676,343) with PMA, $p=0.0002$ (FIG. 8A).

Figure 8C:
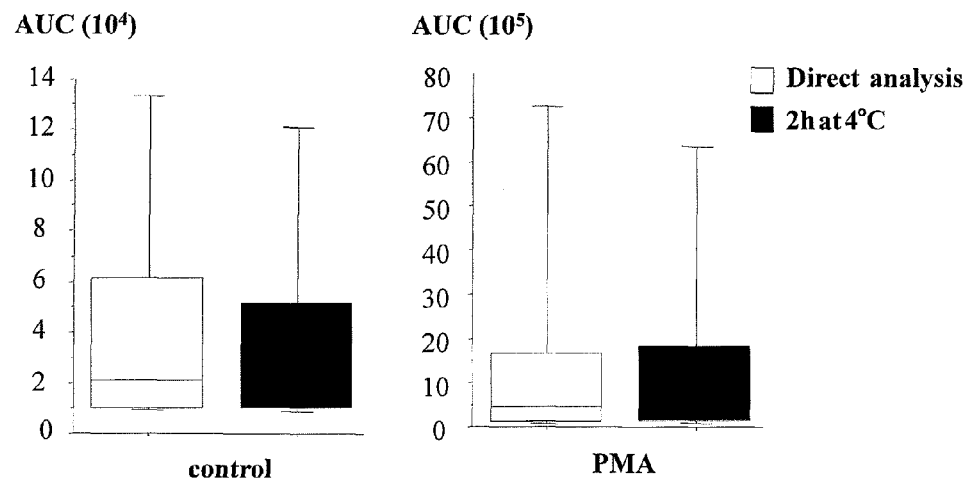

The impact of 2 hrs waiting and of temperature ($-4°$ C.) when performing the simplified protocol was also assessed: 19 samples from 7 patients have been analysed at different times over the EVD period, after 2 hrs of waiting at room temperature (FIG. 8B) or at 4° C. (FIG. 8C). No difference was measured.

Example 4

Examples of Kinetics of Increase and Decrease of ROS in CSF in Case of Infection Materials and Methods The simplified protocol described in Example 2 was used.

Results

The infection status can be monitored by repetitive sampling and analysis of CSF over time. The occurrence of infection was detected by a dramatically increased ROS production. Besides, ROS production decreased quickly after adapted treatment (antibiotics+/−surgery) (FIGS. 9 and 10).

As depicted in FIG. 10, the monitoring of CSF status showed the occurrence of infection at day 10 of the evolution in this patient with EVD, confirmed by microbial analysis. The ROS increase was detected by luminometry in control (A) and stimulated conditions (PMA, B) and by flow cytometry (DHR, C). The administration of antibiotics was followed by a decrease of ROS production, and return to "baseline" detected by both methods. Such a decrease of ROS production was also observed in another patient (patient 1 of FIG. 9) within 24 h after infusion of antibiotics (patient 2 of FIG. 9 is the same patient as shown in FIG. 10).

Example 5

Examples of Reactive Species Produced by Neutrophils, and of Detection Means to Measure their Production in Biological Samples The reactive species produced by neutrophils, which can advantageously be detected according to the invention, are the following:
(i) Reactive Oxygen Species (ROS)
Superoxide anion ($O_2.^-$) is the precursor of a variety of powerful oxidants.
Hydrogen peroxide ($H_2O_2$, in combination with $H^+$, via superoxide dismutase (SOD))
Hypochlorus acid ($ClO^-$, in combination with $Cl^-$, via myeloperoxidase (MPO))
Hydroxyl radical (HO.) from reaction between $O_2.^-$ and Fe or HOCl
Singlet oxygen ($^1O_2$) from reaction between $H_2O_2$ and $OCl^-$.
(ii) Reactive Nitrogen Species (RNS)
NO.
Peroxynitrite anion ($ONOO^-$) from reaction between $O_2.^-$ and NO..

The direct identification of these species has proved to be difficult because their short life spans.

Examples of methods which can be used for ROS and/or RNS detection in the context of the invention are as follows:
(i) Fluorometric
Hydroethidine (dihydroethidium; HE): intracellular reaction with $O_2.^-$. Can be also oxidized by $H_2O_2$.
Scopoletin (7-Hydroxy-6-methoxy-coumarin): substrate for peroxidase (MPO, HRP) with $H_2O_2$ (intra & extra-cellular).
Amplex red (N-Acetyl-3,7-dihydroxyphenoxazine): oxidized by $H_2O_2$ in presence of HRP (extracellular).
DHR (Dihydrorhodamine): intracellular. Reaction with $H_2O_2$. Can also be oxidized by $ONOO^-$ or RNS.
DCFH (2',7'-Dichlorodihydrofluorescein): oxidized by variety of ROS as HO. or ROO. or RNS as NO. or $ONOO^-$.
HPF and APF: detection of HO., $ONOO^-$ or HOCl.
SNAPF (Sulfonaphthoaminophenyl fluorecein): selectively detects HOCl. Intracellular.
DAF (Diaminofluoresceins): NO. probes but also $ONOO^-$.
GFP (Green fluorescent protein *E. coli*): detection of quenching by HOCL, ONOOH and $NO._2$.
(ii) Chemiluminometric (by Scintillation Counters or by Luminometers)
Amplification by chemiluminescence probes
Lucigenin: reduces by $O_2.^-$, independent to MPO.
Luminol: several ROS are reacting. Probably majority of $O_2.^-$ produced by NADPHoxidase. Even extracellular $H_2O_2$.
Isoluminol: extracellular release of ROS ($+++O_2.^-$), less lipophilic than luminol.
L-012: $O_2.^-$, $H_2O_2$, and HO.
MCLA: specific detector of extracellular $O_2.^-$.
Pholasin: realtime kinetic of $O_2.^-$ release.
(iii) Colorimetric
Cytochrome c: simplest detector probe for ROS detection, but low sensitivity. Extracellular $O_2.^-$.
Tetrazolium salts: $O_2.^-$ detection, intra- or extracellular, depending on the salt.
MCD (Monochlorodimedon): formation of HOCl by MPO.

TMB (tetramethylbenzidine): detection of $H_2O_2$ to HOCl conversion, oxidized by HOCl.
Taurine: react with HOCl.
DPA (Diphenylanthracene): intracellular production of $^1O_2$.
$HbO_2/MbO_2$: reacting with NO. forming MetHb and MetMb.

Example 6

Measurement of the Production of Reactive Oxygen Species by Neutrophils in Cerebrospinal Fluid Nosocomial Infection, in Two Novel Cohorts 6.1 Introduction Nosocomial bacterial meningitis is a possible complication after intracranial surgery or trauma and constitutes a daily major concern in the management of these patients.

Ideally, a rapid CSF diagnostic analysis guides the clinician to a decision. However, neither CSF count of cells, concentrations of protein or glucose allow to clearly distinguish a bacterial from an aseptic meningitis (Working Party of the British Society for Antimicrobial Chemotherapy, 2000; Ross et al., 1988; Zarrouk et al., 2007). Aseptic meningitis is frequent in this nosocomial context corresponding to the presence of blood or inflammation in CSF (high leukocyte count, low glucose and high protein level) but not attributable to intracranial infection (negative microbial analyses). Until now, the gold standard diagnostic method for bacterial meningitis is the microbial positivity, which can be obtained at the direct examination or after at least 24 hours of culture.

6.1.1 Nosocomial Meningitis

In a nosocomial context, the term meningitis implies "meningeal inflammation", which may result from invasive surgical procedure, traumatic mechanism and presence of foreign material or infection. If symptoms in community acquired meningitis (headache, fever, neck stiffness, nausea, vomiting and sometimes altered level of consciousness) are easy to recognize, this can be more difficult in the context of brain injury, neurosurgery, brain trauma etc. Globally, there is no consensus definition of "nosocomial bacterial meningitis" and definitions vary throughout literature. On the basis of the gold standard microbial diagnostic method, several studies have broadened this definition with systems of classification. The recent review (2002) by Lozier et al. (Lozier et al., 2002) showed an incidence of ventriculostomy-related infections (VRI) varying from 0 to 22% in relation with the definition used. The Authors proposed a new classification system based on items association:
  Contamination: positive culture+normal CSF glucose, protein and cell count
  Ventriculostomy colonization: multiple positive cultures+normal CSF glucose, protein and cell count+lack of symptoms except fever
  Suspected VRI: negative culture+declined CSF glucose+raised CSF protein and cell count
  VRI: at least one positive CSF culture+declined CSF glucose+raised CSF protein and cell count+symptoms
  Ventriculitis: low glucose+high protein+raised cell count+fever+symptoms In bacterial meningitis, the most common bacteria found in CSF culture are gram-positive cocci consistent with skin flora such as *Staphylococcus epidermidis* (Lozier et al., 2002) and gram-negative bacilli such as *Escherichia coli* (Working Party of the British Society for Antimicrobial Chemotherapy, 2000). These epidemiological data explain the use of large spectrum antimicrobial therapy that has to take into account the local ecology.

Aseptic, or chemical meningitis occurs in 60 to 75% of postoperative cases of meningitis (Zarrouk et al., 2007) and result from the presence of meningeal irritating foreign substances in the subarachnoid space. These substances can be blood or blood degradation products, or actors released by dural substitutes (Working Party of the British Society for Antimicrobial Chemotherapy, 2000) A treatment by high dose of corticosteroid to reduce the meningeal inflammation may prevent the long-term complications, such as adhesive arachnoiditis and hydrocephalus (Ross et al., 1988).

Although bacterial meningitis usually gives more severe symptoms than aseptic, a large spectrum of symptom intensity may overlap with aseptic meningitis (Working Party of the British Society for Antimicrobial Chemotherapy, 2000; Ross et al., 1988; Zarrouk et al., 2007). Consequently, CSF is always put in culture, and a Gram staining is performed together with cell count and measure of concentration of glucose and protein. The interpretation of the results for these CSF items might be difficult in case of subarachnoid haemorrhage that induces confounding presence of blood leukocytes (Working Party of the British Society for Antimicrobial Chemotherapy, 2000).

For the last decades, a reliable test able to distinguish aseptic from bacterial meningitis was investigated. In 1988, lactate, C-reactive protein, chloride, lysozyme, ferritin and so forth were proposed as possible biomarkers (Ross et al., 1988). Various methods combining different criteria have also been tested (Ross et al., 1988). One of the most promising methods for the typology of these patients was named the "cell index". This cell index is the ratio of leukocytes over erythrocytes in CSF divided by the same ratio in peripheral blood (Pfausler et al., 2004). Another promising method consisted of measuring the lactate concentration in CSF (Leib et al., 1999). Until now, none of these methods reached a sufficient sensitivity nor specificity to be applied universally.

6.1.2 Production of ROS

Among the first line of defence against bacteria, the polymorphonuclear neutrophils (PMNs) play a major role in the innate immune system. In healthy conditions, circulating PMNs are in a quiescent state. When an infection or a tissue inflammation occurs, the release of mediators attracts PMNs to the site by crossing the vascular barrier. At site they participate in bacteria elimination by both phagocytosis and oxidative burst. The later results from a large production of reactive oxygen species (ROS) inside the phagosomes.

The key enzyme for ROS synthesis and then release is the NADPH oxidase, a complex enzymatic protein containing several subunits. In normal conditions, the enzyme is slightly working, being ready to synthesize large amount of ROS when a signal as the presence of bacteria or of an inflammatory polypeptide is active. This signal leads under PKC to phosphorylate the subunits that are assembled to the membrane, producing superoxide radical ($O_2.^-$) in presence of oxygen and NADPH substrate (Freitas et al., 2009; Kerkhoff et al., 2005). NADPH is produced by the hexose monophosphate shunt (HMPS), an alternative glycolysis pathway. After a passive entry in phagocyte, glucose is engaged in this pathway through the oxidation of one molecule of glucose-6-phosphate, forming two molecules of NADPH. The consumption of NADPH activates the HMPS indirectly through a feedback system. It has been shown that HMPS activity could be stimulated by phorbol 12-myriaste 13-acetate (PMA) (Klassen et al., 1982). PMA amplifies the PKC pathway (Blagosklonny et al., 1997) that phosphorylses some of the subunits of NADPH oxidase, increasing the produced amount of ROS and activating HMPS in order to get more substrates. Therefore PMA is a membrane-active stimulator of oxidative metabolism commonly used to study the ROS production (Klassen et al., 1982).

To measure the oxidative burst or the amount of ROS produced, there are several well-established methods. These methods use a number of different techniques such as fluorimetric, chemiluminometric and colorimetric probes (Freitas et al., 2009). The method chosen in this study is the chemiluminometric with luminol, using the protocol described in Example 3 above.

6.2. Objective

In this observational study, the production of ROS by cells in CSF was measured, as a functional evaluation of PMNs associated with meningitis from bacterial origin or not. The hypothesis was that CSF PMNs activation induced by infection releases more ROS than other aetiologies. The production of ROS was quantified using luminescence (luminol and luminometry). Results were later compared with the microbiological findings as well as to the results of the conventional analyses on CSF. Finally, ROS measurements were tested for the prediction of bacterial or aseptic meningitis.

All included patients had recently been operated, suffered a trauma or had an external ventricular drain (EVD). In this nosocomial context, the causing pathogens were usually bacteria present on skin or scalp or inside skull cavities (air-filled sinuses and mastoid bone), penetrating into the intracranial space because of intra-extra cranial communication, leak or device (Working Party of the British Society for Antimicrobial Chemotherapy, 2000). Therefore this study did not include viral meningitis. In addition to this, the impact of bacteria's phenotype was not considered in this analysis, because of the small number of cases and the common mechanisms of phagocytosis implicated.

6.3. Methodology 6.3.1 Study Design

The study contained two parts based on two cohorts, hereby referred to as training and testing cohort. The training cohort contained relevant samples collected during 2009 and 2010 for the purpose of evaluating the technique. The testing cohort on the other hand is the first part of an on-going multicentre study intending to test the technique on approximately 130 patients with a suspicion of meningitis. There were no differences in the lab techniques between the two periods, but the inclusion criteria for sampling were not as well defined in the first as in the second period. Also for the testing cohort, the clinician could provide the needed clinical parameters already at the time of collection. Results from the analyses made on the bigger training cohort could then be compared to the testing cohort.

6.3.2 Training Cohort

Patients

Samples of CSF were collected between the 12 Feb. 2009 and the 13 Oct. 2010. At the time the technique was still being evaluated so samples were collected on a broad basis. Those that were collected at the moment of suspicion of meningitis were selected and analysed. The inclusion criteria used were a sign of inflammation, with either a temperature superior to 38.0° C. or a blood leukocyte count superior to $12*10^9/l$ or inferior to $4*10^9/l$. Furthermore the patient should not have been started on antibiotics, of a sufficient dose to treat meningitis. Samples were collected from catheters (external ventricular drain (EVD) and external lumbar shunt (ELS)) as well as by lumbar puncture (LP). After the sampling the investigators did not take any part in the prescription of treatment.

The included patients were divided into five different categories on the basis of their initial clinical context. These categories were intracranial haemorrhage requiring EVD, trauma, post-operative, hydrocephaly and community-acquired infection.

Experimental Laboratory Protocol

The laboratory testing was made in two conditions; one stimulated and one without stimulation (control). When CSF amount was sufficient, measurements of both conditions were made in duplicate, making a total of four test tubes. If CSF volume was not sufficient, the control condition was prioritised. To each test tube 550 µl of the buffer Hanks' Balanced Salt Solution (HBSS, Invitrogen, Cergy-Pontoise, France), 250 µl of CSF and 100 µl of a solution of luminol (50 µM, Sigma, Saint Quentin Fallavier, France) were added. The test tubes were then incubated at 37° C. for 10 minutes, in the dark. After incubation, 100 µl of the agonist phorbol 12-myristate 13-acetate (PMA, Sigma) ($10^{-6}$M) was added to the two "stimulated" tubes and 100 µl HBSS to the "control" tubes. Then the four tubes were put in the luminometer (Berthold Technologies' Auto Lumat Pus LB 953), where the emitted light intensity was measured during one second, every minute for 20 minutes. The signal was converted by a combined computer with specialized software, and results were directly presented in an Excel table and in a graph, in light intensity (Relative Light Units (RLU)) in function of time. Using the produced graph the Area under the curve (AUC), for the stimulated and control condition, was calculated and later compared between samples. All collected samples were analysed in the same laboratory (research laboratory of Pr Payen at Hôpital Lariboisière, EA 3509, Université Paris 7 Diderot) using the same luminometer. All collected samples were analysed at most two hours after their collection.

Retrospectively, the general information needed for the analyses was gathered by going through casebooks and results from bacteriology, biochemistry and haematology. In bacteriology the CSF was gram coloured for direct examination and cultivated for five days in a solid and a liquid environment. The number of elements per $mm^3$ was counted by the use of a Cell of Malassez and May Grunwald Giemsa colouring. In biochemistry, the CSF concentration of protein was assessed with turbidimetry and that of glucose with an enzymatic reaction both using Abbott Architect C8000, Rungis, France. In haematology, the white blood cell count was calculated with flow cytometry using Cell Dyn Sapphire, Abbott, Rungis, France.

Analysis and Statistics

At a point during the analysis an external group of investigators, with clinical experience, were consulted regarding the classification of patients. Based on the previous referred literature, with some justifications for the broad inclusion criteria of patients, the definitions of the groups used in the analysis were chosen to:

Septic meningitis: positive bacteriological culture together with CSF leukocytosis Aseptic meningitis: negative bacteriological culture but CSF leukocytosis Contamination: positive bacteriological culture without CSF leukocytosis Non-septic CSF: all the cases that are not septic, including aseptic, contamination and negatives Negatives: negative bacteriological culture without CSF leukocytosis Where CSF leukocytosis was defined as:

White blood cell count in CSF $>100/mm^3$
and/or
% PMN in CSF >50%

With these definitions, three types of analyses were made. The first compared CSF leukocytosis with no leukocytosis, the second compared the cases of septic with non-septic meningitis and the third compared septic with aseptic meningitis.

Statistical results were expressed as mean, standard deviation, median, odds ratio and interquartile range (IR, first and third quartiles) or counts and percent. The characteristics of the various groups defined above were compared. As, in some cases, there was more than one sample per subject, to avoid bias linked to intra-subject correlation, comparisons were made with a generalized estimation equation model including a cluster effect, where the cluster was defined as a subject (Liang and Zeger, 1986; Zeger and Liang, 1986). To assess the accuracy of different predictive scores, Receiver Operating Characteristics (ROC) curves were presented with their estimated area under the curve (AUC). All tests were two-sided at the 0.05 significance level. Analyses were performed using R statistical package (online at http://www.R-project.org).

6.3.3 Testing cohort

Patients

From the 14 Oct. 2010 till the 10 Dec. 2010, 21 patients were included from two units (intensive care and neurosurgery) at Hopital Lariboisiere, Paris. The following criteria were obtained: 1) suspicion of nosocomial meningitis following intracranial or spinal surgery or trauma, 2) febrile (>38° C.), 3) older than 18 years and 4) not yet treated with antibiotics of sufficient dose to treat meningitis. Medical management was completely independent from the results of the tested method. The sample of CSF was collected on the same time as the classical biochemical and microbial analyses.

Experimental Laboratory Protocol

The laboratory testing was performed in the same way as for the training cohort. While these samples were collected, the physicians responsible for the patient filled in a form with some general information (Appendix 2). This information included; the patient's maximal temperature and lowest Glasgow Coma Scale for the last 24 hours, clinical context, results from microbiological and biochemical analyses of CSF and blood as well as current treatment.

Analysis and Statistics

The analysis on the testing cohort was made using the same definitions as those used for the training cohort. The chosen thresholds of ROS production from the training cohort were then applied on the results of the testing cohort.

6.4. Ethical Aspects

The Institutional Review Board, IRB 00006477, approved experiments on the training cohort on the 28 Jun. 2008, no 08-475. The testing cohort obtained ethical approval on the 17 Sep. 2010, no 10-071. Samples of 1 ml of CSF were collected only when clinically indicated and on the same time as those for bacteriology and biochemistry, causing no unnecessary harm to the patient. In order to avoid an interference with research findings, the clinician in charge of the patient was not informed of the results and the investigators did not take any part in the following or treatment of the patients. The recruited patients were informed of the study through a detailed letter. The analysis of the results was blinded with patients given a combination of letters and figures.

6.5. Results 6.5.1 Training Cohort

Selection of the Cohort

During the study period, 133 measurements were made. Excluded from the analysis were 28 measurements made under antibiotics at a sufficient dose to treat meningitis, 14 because of missing data, 12 out of inflammatory context (absence of fever and white blood cell count inferior to 12 000/$mm^3$) and one because of traumatic LP. In the end, out of the 133 measurements performed, 78 were analysed, coming from 59 patients.

Out of the 78 samples being analysed, 10 met criteria of septic meningitis, 28 of aseptic meningitis, 4 of contaminations and 36 samples had a negative culture and lacked CSF leukocytosis. 40 out of the 78 samples were collected by LP, two from external lumbar shunt (ELS) and the rest from EVD. Five of the samples were taken from patients treated with hydrocortisone, but none were under glucocorticoids.

The initial clinical context of the samples were divided between 29 cases of intracranial haemorrhage requiring EVD, 13 traumas, 27 cases of postoperative, 3 of hydrocephaly and 6 cases of community-acquired infections requiring EVD.

ROS Production and CSF Leukocytosis

Table 5 summarizes all the variables tested according to CSF leukocytosis or septic meningitis. When the cases of CSF leukocytosis (>100 leukocytes/mm$^3$ or >50% of PMNs) were compared to the cases with no leukocytosis (<100 leukocytes/mm$^3$ and <50% of PMNs), both stimulated (AUC PMA; 2050 versus 98) and spontaneous (AUC CONT; 41 versus 13) ROS production were significantly different (p<0.01). The difference between those groups was significant for all of the measured parameters except for the white blood cell count in blood.

For testing ROS measurements with leukocytosis in CSF, ROC curves generated by cross validation provided indications for sensitivity and specificity. These curves are shown in FIG. 11. For this purpose the PMA stimulated condition gave a higher area under the curve (AUC) of the ROC curve of 0.849 compared to control condition of 0.729.

TABLE 5

Results of the cohort divided according to CSF leukocytosis or septic meningitis.
Results are expressed as median and the interquartile range (in brackets).

| | | CSF leukocytosis | | | | Septic meningitis | | | |
|---|---|---|---|---|---|---|---|---|---|
| | All (n = 78) | Leukocytosis (n = 38) | No leukocytosis (n = 40) | OR [95% CI] | p | Septic (n = 10) | Non septic (n = 68) | OR [95% CI] | p |
| Maximal Temp (° C.) | 38.6 (38.2 to 39.2) | 39 (38.6 to 39.9) | 38.4 (38.2 to 38.8) | 1.1501 [1.0155; 1.3026] | 0.03* | 40 (38.6 to 40.5) | 38.6 (38.2 to 39.1) | 1.123 [1.0149; 1.2426] | 0.02* |
| WBC count 0$^3$/mm$^3$) | 13.5 (9.7 to 17.2) | 14 (12.3 to 18.5) | 13.2 (9.5 to 15.6) | 1.003 [0.984; 1.0224] | 0.76 | 21.6 (17.1 to 24.6) | 13.1 (9.6 to 15.6) | 1.0118 [0.9933; 1.0305] | 0.21 |
| % blood PMNs | 81 (75 to 85) | 84 (78 to 86) | 78 (73 to 81) | 1.0238 [1.0082; 1.0397] | <0.01* | 86 (83 to 90) | 79 (73 to 84) | 1.0167 [1.0015; 1.032] | 0.03* |
| AUC PMA (10$^3$RLU) | 749 (94 to 3652) | 2050 (1049 to 50073) | 98 (43 to 679) | 1.0003 [1.0001; 1.0005] | <0.01* | 3875 (1071 to 50073) | 617 (71 to 2484) | 1.0001 [0.9999; 1.0002] | 0.43 |
| AUC CONT 0$^3$RLU) | 23 (9 to 95) | 41 (13 to 327) | 13 (80 to 29) | 1.0004 [1.0002; 1.0006] | <0.01* | 261 (69 to 2598) | 17 (9 to 47) | 1.0004 [1.0002; 1.0005] | <0.01* |
| CSF cell count (per mm$^3$) | 30 (8 to 368) | 395 (83 to 1813) | 8 (2 to 22) | 1.0005 [1.0001; 1.0009] | <0.01* | 500 (310 to 1958) | 23 (7 to 158) | 1.0001 [0.9998; 1.0005] | 0.40 |
| % CSF PMNs | 10 (0 to 83) | 84 (69 to 92) | 0 (0 to 2) | 1.011 [1.0099; 1.0121] | <0.01* | 87 (68 to 93) | 4 (0 to 75) | 1.0027 [1.0005; 1.0049] | 0.02* |
| CSF glucose (mmol/l) | 3.9 (2.5 to 5) | 3.2 (2 to 4.3) | 4.4 (3.2 to 5.6) | 0.8943 [0.8367; 0.9558] | <0.01* | 2.5 (1.8 to 3.5) | 4 (2.8 to 5) | 0.9748 [0.9244; 1.0279] | 0.35 |
| CSF protein (g/l) | 0.8 (0.5 to 1.7) | 1.2 (0.7 to 3.1) | 0.6 (0.4 to 1) | 1.052 [1.0203; 1.0846] | <0.01* | 2.2 (1.1 to 5.3) | 0.8 (0.5 to 1.3) | 1.0211 [0.9814; 1.0623] | 0.30 |
| CSF blood glucose ratio | 0.5 (0.4 to 0.6) | 0.4 (0.3 to 0.5) | 0.6 (0.4 to 0.7) | 0.3623 [0.2232; 0.5879] | 0.00* | 0.4 (0.3 to 0.5) | 0.5 (0.4 to 0.7) | 0.8162 [0.5722; 1.1642] | 0.26 |

WBC = White blood cell;
PMNs = polymorph nuclear neutrophils;
AUC = area under curve;
RLU = Relative light units;
CSF = cerebrospinal fluid;
OR = odds ratio;
CI = confidence interval;
* = p < 0.05
AUC PMA was tested per 100,000 units; AUC CONT per 5000 units; cell count in CSF per 10 cell Out of the given results of the AUC PMA a threshold of 748860 RLU was chosen showing the best couple of specificity (76%) and sensitivity (78%). Table 6 shows the repartition of the samples according to this threshold for prediction of CSF leukocytosis. For these analyses there were 7 (18%) false negative and 9 (23%) false positive.

TABLE 6

The number of cases of CSF leukocytosis with an AUC PMA (stimulated condition) over and under the chosen threshold of 748860 RLU.

| Threshold: 748860 | CSF leukocytosis (n = 38) | No CSF leukocytosis (n = 40) |
|---|---|---|
| Over threshold | 31 | 9 |
| Under threshold | 7 | 31 |

CSF leukocytosis = CSF with >100 leukocytes or >50% PMNs.
RLU = Relative light units.

ROS Production and Septic Meningitis

When septic and non-septic CSF were compared, four parameters were found to differ significantly: the maximal temperature, the % blood PMNs, the AUC CONT and the % PMN in CSF, as seen in Table 5. For the purpose of diagnosis of the presence of bacteria, the AUC CONT was superior to that of PMA, see FIG. 12. This also means that in this study none of the normally used parameters, except for % CSF PMNs, were significantly different between the septic and the non-septic cases.

When it comes to the distinction between septic and non-septic meningitis, the threshold of AUC CONT was chosen at 57,195 RLU with a specificity of 75% and a sensitivity of 80%. Table 7 shows that the test misdiagnoses 20% (false negative) of the septic and 25% of the non-septic cases.

TABLE 7

The number of septic meningitis versus non-septic CSF with an AUC CONT (control condition) over and under the threshold of 57 195 RLU.

| Threshold: 57195 | Septic (n = 10) | Non-septic (n = 68) |
|---|---|---|
| Over threshold | 8 | 17 |
| Under threshold | 2 | 51 |

Non-septic CSF includes aseptic meningitis and negative CSF.
RLU = Relative light units.

Comparison of Septic Versus Aseptic Meningitis

When the 10 cases of septic meningitis were compared to the 28 aseptic meningitis (CSF leukocytosis with negative culture), there was a significant difference (p=0.0015) in the measurements of AUC CONT median of 260,618 (IR: 69,349-2,598,484) versus 30,383 (IR: 11,197-244,937)).

6.5.2 Testing Cohort

Out of the 21 samples (from 16 patients) that were analysed, there was one case of septic meningitis, one contamination, 13 aseptic and 6 negative samples. Table 8a and 8b depict the repartition of samples applying the given thresholds from the training cohort. The 8 cases of CSF leukocytosis were above the chosen threshold, but so were 71% of samples lacking CSF leukocytosis. The only case of septic meningitis was also over the thresholds, as well as 65% of the non-septic cases.

TABLE 8

| | Threshold: 748860 | CSF leukocytosis (n = 8) | No CSF leukocytosis (n = 7) |
|---|---|---|---|
| a | Over threshold | 8 | 5 |
|   | Under threshold | 0 | 2 |
| | Threshold: 57195 | Septic (n = 1) | Non-septic (n = 20) |
| b | Over threshold | 1 | 13 |
|   | Under threshold | 0 | 7 | a: The number of cases of CSF leukocytosis with an AUC PMA (stimulated condition) over and under the chosen threshold. The total number of measurements of AUC PMA was 15, because of insufficient volume of CSF for 6 of the samples.
b: The number of cases of septic versus non-septic meningitis with an AUC CONT (control condition) over and under the threshold.
CSF leukocytosis = CSF with >100 leukocytes or >50% PMNs;
AUC = area under curve;
Non-septic CSF including aseptic and negative CSF.

6.5.3 Evolution of ROS Production after Initiation of Antibiotics

Among samples from the training cohort, data related to the evolution of the ROS production under treatment were extracted. FIG. 13 shows the evolution for a patient with meningitis of *Pseudomonas aeruginosa* in the context of intracranial haemorrhage requiring EVD. After the initial sample made for diagnosis of septic meningitis (D0) the treatment was initiated and later CSF controls, after three and six days, showed that the amount of ROS had nicely diminished as the cultures were negative.

A second patient never had a CSF positive culture, but because the evolution of leukocytosis in CSF (D-2 with 42 cells to D0 with 9900 cells), the clinicians were convinced that they had to give antibiotics. The ROS production declined along time under treatment, suggesting its efficiency. We can notice that the ROS production had passed the positive threshold for septic meningitis, already at the time of the first sample.

6.6. Discussion

The objective of the study was to measure the production of ROS in the case of suspicion of meningitis to try to diagnose bacterial meningitis in a post-interventional context (postoperative or trauma). The results of the training cohort demonstrated that PMA-stimulated and spontaneous production of ROS were elevated in cases with CSF leukocytosis. The stimulated condition (PMA) represented the best measurement for diagnosis of leukocytosis with an area under ROC curve at 0.849 and a sensitivity of 78% and specificity of 76% for a threshold of 748,860 RLU. The spontaneous production of ROS (control) was higher when bacteria were present in CSF, with a ROS curve area of 0.793, sensitivity of 80% and specificity of 75% for a threshold of 57,195 RLU. These results suggest that the non-stimulated condition could be of interest for detecting bacterial meningitis. Applying thresholds from the training cohort to the testing cohort allowed to detect the eight cases of CSF leukocytosis and the only case of septic meningitis. The easiness, rapidity, and low cost of this test can help the clinician to screen CSF samples before sending them to the microbiological laboratory and initiating the antimicrobial therapy.

With the training cohort, quite a large group of patients were analyzed after ethical acceptance. The tested patients presented a large diversity of clinical context, with a large range of delay for intervention and various sampling ways. Such diversity reflected the clinical routine practice with a minimum of exclusion criteria.

The on-going testing cohort is too small at time of report to draw any conclusion. Interestingly, applying the training cohort results, the case having positive culture was detected by the test, although the majority of the cases with negative bacteria also were above the thresholds. There were no false negative samples in this cohort.

The ROS production data correlated well with the presence of PMNs in samples, which may result from activation of NADPH oxidase (Freitas et al., 2009). This concept is also corroborated by the fast decline in ROS production after the initiation of antibiotic treatment (FIG. 14), with a decrease in CSF PMNs. The correlation between PMA-stimulated condition and the leukocytosis in CSF make the test interesting in screening CSF samples for suspicions of meningitis. This test may determine the possible candidates for septic meningitis and thereby reduce the amount of samples needed to be cultivated in microbiological laboratory. The spontaneous ROS production on the other hand could be used to screen suspicions of bacterial meningitis. This could determine the candidates for immediate antibiotic therapy and possibly reduce the administration of unnecessary antibiotics.

The two false negative samples found when using the threshold of AUC CONT to predict the presence of bacteria (Table 7), had a RLU largely under the chosen threshold of 57,195 RLU (11,040 and 10,185 RLU). This may perhaps be explained by the fact that the test is based on the function of the PMNs. The studied PMNs in these samples could have been "exhausted", which would also make them unable to normally respond to PMA. This could have been the case for one sample (465,450 RLU), considering the chosen threshold (748,860 RLU).

Seventeen false positive samples with a high spontaneous ROS production but without bacteria were found (Table 7). Nine of these tests were sampled from patients under antibiotics, given for other infective sites than intracranial, which might have altered the microbiological results of CSF culture. The numerous false positive samples especially found in the testing cohort bring up the question of the sensitivity of the test related to the chosen threshold. In this context of infection, a clinician would prefer a high sensitivity to a high specificity, because antibiotics given in excess are still a non-dangerous treatment. Since positive samples have to be detected, a few false positives cases are acceptable. The classically used methods combining clinic and biology (CSF cell count, protein and glucose concentrations) were not more accurate in this study (Table 5) and they are more complex and more demanding, because they require a number of analyses from different laboratories. The method proposed herein can help to rationalise the demand for analyses and antibiotic therapy, which is clinically useful. In addition, the rationalisation of antibiotic administration could be beneficial for the ecology of care units, especially by diminishing the use of large spectrum antibiotics. It may also limit the invasive procedures for intravenous administration of drugs and/or replacement of devices for CSF drainage.

To validate a biomarker, Marshall et al claimed that three domains have to be proven (Marshall and Reinhart, 2009). First of all it must be demonstrated that the assay truly measures a particular molecular activity or its relevant biological activity. Secondly, the biomarker must discriminate patients with the disease from those without. Last but not least, the measurement of the biomarker should help in a clinical decision that leads to improved outcome for the patient. For the hereby-considered biomarker, the first condition is demonstrated by the high correlation between stimulated condition and CSF leukocytosis, making luminometry, in the stimulated condition, a good technique for measuring the level of meningeal inflammation. The second is demonstrated by the significant difference of AUC CONT between septic and aseptic meningitis. The third domain is demonstrated when a negative measurement leads to an avoidance of unnecessary antibiotics.

One of the shortcomings of this study is the large diversity of samples, making it harder to draw general conclusions. The site of sampling might also affect the results. For example in one case the patient was suffering from an empyema enclosing the infection, which was therefore not detectable with a LP sampling. In this case the method presented herein detected this activity, proving the importance of a high sensibility. Another shortcoming is the fact that the "gold standards" used as reference for our method had limits of their own. The cells of the CSF are manually counted with potential errors due to the phenotype. The bacteriological culture also has its limits, especially when the patient already received antibiotics for another infection, even if non sufficient to treat a meningitis. Cultures might also be negative because of sampling in a non-representative area. This could be the case for the patient whose evolution after treatment is shown in FIG. 14.

The technique described herein can advantageously be applied also for detecting community-acquired meningitis, where the problem of distinguishing bacterial from viral meningitis is much larger. Lymphocytes do not have the machinery for ROS production by NADPH oxidase and CSF lymphocytosis related to virus infection will not give a positive signal. Theoretically, these different types of infections will hence be differentiated with this method since the immune system reacts differently to bacteria and viruses.

Finally, it is to be noted that the present method will be even more useful when it is transferred to a very easy technique, similar to a urine test strip. Then one will simply dip the strip in the CSF and the answer will guide the clinician in his difficult interpretation of clinic. For such an easy test, the result does not have to be perfect but the higher the sensitivity, the better it is.

6.7. Conclusions

Analyses of a training cohort showed that the PMA-stimulated ROS production was elevated in the presence of CSF leukocytosis. It was also seen that cases of septic meningitis had a raised spontaneous production compared to the rest of the samples. When the thresholds from these analyses, obtained from the training cohort, were applied on the testing cohort, the eight cases of CSF leukocytosis and the only septic meningitis were detectable. This test is thus of interest for screening CSF and determining the presence of CSF leukocytosis and septic meningitis.

Example 7

Stability of the Ability of Cells to Produce ROS after Sample Collection

In order to assess whether a sample has to be tested immediately after collection, or if a delay of a few hours between sample collection and testing is acceptable, the same sample has been tested for ROS production, in both control and activated conditions, immediately after collection and after 1, 2, 4, 6 and 8 hours of storage at room temperature.

The results, shown in Table 9 below, show that the samples can be kept a few hours without significant impact on the results. This enables to send a sample to a laboratory far from the place where it has been collected, and/or to keep it overnight when it has been collected late at night. The important feature, which must always be respected, is that the sample must not be frozen, since this would kill the cells.

TABLE 9

ROS production from the same sample, at different times after sample collection.

| Timing | AUC PMA (RLU) | AUC CONT (RLU) |
| --- | --- | --- |
| H0 | 5418435 | 8175 |
| 1 h | 5703480 | 11430 |
| 2 h | 5443650 | 18675 |
| 4 h | 5625960 | 12300 |
| 6 h | 6126990 | 13515 |
| 8 h | 4925010 | 17340 |

REFERENCES

Blagosklonny, M. V., Prabhu, N. S., and El-Deiry, W. S. (1997) Defects in p21WAF1/CIP1, Rb, and c-myc signaling in phorbol ester-resistant cancer cells. *Cancer Res*, 57, 320-325.

Bota, D. P., Lefranc, F., Vilallobos, H. R., Brimioulle, S, and Vincent, J. L. (2005) Ventriculostomy-related infections in critically ill patients: a 6-year experience. *J Neurosurg*, 103, 468-472.

Cassatella, M. A., Bazzoni, F., Flynn, R. M., Dusi, S., Trinchieri, G. and Rossi, F. (1990) Molecular basis of interferon-gamma and lipopolysaccharide enhancement of phagocyte respiratory burst capability. Studies on the gene expression of several NADPH oxidase components. *J Biol Chem*, 265, 20241-20246.

Working Party of the British Society for Antimicrobial Chemotherapy, (2000) The management of neurosurgical patients with postoperative bacterial or aseptic meningitis or external ventricular drain-associated ventriculitis. Infection in Neurosurgery. *Br J Neurosurg*, 14, 7-12.

Druel, B., Vandenesch, F., Greenland, T., Verneau, V., Grando, J., Salord, F., Christen, R. and Etienne, J. (1996) Aseptic meningitis after neurosurgery: a demonstration of bacterial involvement. *Clin Microbiol Infect*, 1, 230-234.

Fay, A. J., Qian, X., Jan, Y. N. and Jan, L. Y. (2006) SK channels mediate NADPH oxidase-independent reactive oxygen species production and apoptosis in granulocytes. *Proc Natl Acad Sci USA*, 103, 17548-17553.

Forgacs, P., Geyer, C. A. and Freidberg, S. R. (2001) Characterization of chemical meningitis after neurological surgery. *Clin Infect Dis*, 32, 179-185.

Freitas, M., Lima, J. L. and Fernandes, E. (2009) Optical probes for detection and quantification of neutrophils' oxidative burst. A review. *Anal Chim Acta*, 649, 8-23.

Hader, W. J. and Steinbok, P. (2000) The value of routine cultures of the cerebrospinal fluid in patients with external ventricular drains. *Neurosurgery*, 46, 1149-1153; discussion 1153-1145.

Holloway, K. L., Barnes, T., Choi, S., Bullock, R., Marshall, L. F., Eisenberg, H. M., Jane, J. A., Ward, J. D., Young, H. F. and Marmarou, A. (1996) Ventriculostomy infections: the effect of monitoring duration and catheter exchange in 584 patients. *J Neurosurg*, 85, 419-424.

Kerkhoff, C., Nacken, W., Benedyk, M., Dagher, M. C., Sopalla, C. and Doussiere, J. (2005) The arachidonic acid-binding protein S100A8/A9 promotes NADPH oxidase activation by interaction with p67phox and Rac-2. *Faseb J*, 19, 467-469.

Klassen, D. K., Colliding, P. R. and Sagone, A. L., Jr. (1982) Activation of monocyte and granulocyte antibody-dependent cytotoxicity by phorbol myristate acetate. *Infect Immun*, 35, 818-825.

Leib, S. L., Boscacci, R., Gratzl, O. and Zimmerli, W. (1999) Predictive value of cerebrospinal fluid (CSF) lactate level versus CSF/blood glucose ratio for the diagnosis of bacterial meningitis following neurosurgery. *Clin Infect Dis*, 29, 69-74.

Li, Y. and Trush, M. A. (1998) Diphenyleneiodonium, an NAD(P)H oxidase inhibitor, also potently inhibits mitochondrial reactive oxygen species production. *Biochem Biophys Res Commun*, 253, 295-299.

Liang, K. Y. and Zeger, S. L. (1986) Longitudinal Data Analysis Using Generalized Linear Models. *Biometrika*, 73, 13-22.

Lozier, A. P., Sciacca, R. R., Romagnoli, M. F. and Connolly, E. S., Jr. (2002) Ventriculostomy-related infections: a critical review of the literature. *Neurosurgery*, 51, 170-181; discussion 181-172.

Lundqvist-Gustafsson, H. and Bengtsson, T. (1999) Activation of the granule pool of the NADPH oxidase accelerates apoptosis in human neutrophils. *J Leukoc Biol*, 65, 196-204.

Marshall, J. C. and Reinhart, K. (2009) Biomarkers of sepsis. *Crit. Care Med*, 37, 2290-2298.

Mayhall, C. G., Archer, N. H., Lamb, V. A., Spadora, A. C., Baggett, J. W., Ward, J. D. and Narayan, R. K. (1984) Ventriculostomy-related infections. A prospective epidemiologic study. *N Engl J Med*, 310, 553-559.

Pfausler, B., Beer, R., Engelhardt, K., Kemmler, G., Mohsenipour, I. and Schmutzhard, E. (2004) Cell index—a new parameter for the early diagnosis of ventriculostomy (external ventricular drainage)-related ventriculitis in patients with intraventricular hemorrhage? *Acta Neurochir (Wien)*, 146, 477-481.

Piccoli, C., Ria, R., Scrima, R., Cela, O., D'Aprile, A., Boffoli, D., Falzetti, F., Tabilio, A. and Capitanio, N. (2005) Characterization of mitochondrial and extra-mitochondrial oxygen consuming reactions in human hematopoietic stem cells. Novel evidence of the occurrence of NAD(P)H oxidase activity. *J Biol Chem*, 280, 26467-26476.

Ross, D., Rosegay, H. and Pons, V. (1988) Differentiation of aseptic and bacterial meningitis in postoperative neurosurgical patients. *J Neurosurg*, 69, 669-674.

Segal, A. W. (2005) How neutrophils kill microbes. *Annu Rev Immunol*, 23, 197-223.

Serhan, C. N. and Savill, J. (2005) Resolution of inflammation: the beginning programs the end. *Nat Immunol*, 6, 1191-1197.

Tavares, W. M., Machado, A. G., Matushita, H. and Plese, J. P. (2006) CSF markers for diagnosis of bacterial meningitis in neurosurgical postoperative patients. *Arq Neuropsiquiatr*, 64, 592-595.

Trabold, B., Gruber, M. and Frohlich, D. (2007) Synthetic inotropes inhibit the expression of adhesion molecules and augment the expression of L-selectin in polymorphonuclear neutrophils. *Resuscitation*, 74, 352-356.

Zarrouk, V., Vassor, I., Bert, F., Bouccara, D., Kalamarides, M., Bendersky, N., Redondo, A., Sterkers, O. and Fantin, B. (2007) Evaluation of the management of postoperative aseptic meningitis. *Clin Infect Dis*, 44, 1555-1559.

Zeger, S. L. and Liang, K. Y. (1986) Longitudinal data analysis for discrete and continuous outcomes. *Biometrics*, 42, 121-130.

The invention claimed is:

1. A method for in vitro diagnosing a meningitis in cerebrospinal fluid to distinguish between septic and aseptic meningitis, wherein said method comprises:
   a) stimulating polymorphonuclear neutrophils (PMNs) present in a sample of said cerebrospinal fluid collected from a subject with an agonist of NADPH oxidase; and
   b) measuring the reactive oxygen species (ROS) produced by polymorphonuclear neutrophils (PMNs) present in the sample of cerebrospinal fluid after stimulation by the NADPH oxidase agonist using a chemiluminescent probe or a colorimetric reagent the color of which changes in presence of ROS, wherein the measure of ROS production by the PMNs present in the sample of cerebrospinal fluid is performed at most eight hours after sample collection, and wherein a ROS production above a predetermined threshold is indicative of a septic meningitis and non-indicative of aseptic meningitis.

2. The method of claim 1, wherein the cerebrospinal fluid sample is from a patient in a situation selected from the group consisting of brain trauma, invasive intracranial procedures and suspected community meningitis.

3. The method of claim 1, comprising the steps of
   (i) measuring the level of ROS spontaneously produced by the PMNs present in the sample of cerebrospinal fluid, and
   (ii) measuring the level of ROS produced by the PMNs present in the sample of cerebrospinal fluid after stimulation by an agonist of NADPH oxidase,
   wherein:
   a) if the level measured in step (i) is below a first predetermined threshold and the level measured in step (ii) is below a second predetermined threshold, it can be concluded that there is no bacterial infection in the cerebrospinal fluid;
b) if the level measured in step (i) is above a first predetermined threshold, a bacteriological analysis of the sample is performed; and
c) if the level measured in step (ii) is above a second predetermined threshold, a bacteriological analysis of the sample is performed.

4. The method of claim 3, wherein if the level measured in step (i) is above a first predetermined threshold, decision is made to treat the patient with antibiotics without waiting the result of bacterial analysis.

5. The method according to claim 1, for in vitro following the efficiency of an antibiotic treatment in a patient having a septic meningitis in the cerebrospinal fluid, comprising a step of measuring, in a sample of said fluid, the production of radical oxygen species (ROS) after stimulation by the agonist of NADPH oxidase, wherein a decrease in ROS production after the beginning of the antibiotic treatment indicates that said treatment is appropriate.

6. The method according to claim 1, for in vitro detecting a treatment failure, comprising a step of measuring the production of radical oxygen species (ROS) after stimulation by the agonist of NADPH oxidase in a cerebrospinal fluid sample collected after the beginning of said treatment, wherein a ROS production above a predetermined threshold in said sample is indicative of treatment failure.

7. The method of claim 1, wherein the agonist of NADPH oxidase is phorbol 12-meristate 13-acetate (PMA).

8. The method of claim 1, wherein the colorimetric reagent is on a testing strip.

* * * * *